United States Patent
Kahook

(10) Patent No.: US 10,327,947 B2
(45) Date of Patent: Jun. 25, 2019

(54) MODIFIED DUAL-BLADE CUTTING SYSTEM

(71) Applicant: THE REGENTS OF THE UNIVERSITY OF COLORADO, A BODY CORPORATE, Denver, CO (US)

(72) Inventor: Malik Y Kahook, Denver, CO (US)

(73) Assignee: THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 927 days.

(21) Appl. No.: 14/375,350

(22) PCT Filed: Apr. 19, 2013

(86) PCT No.: PCT/US2013/037374
§ 371 (c)(1),
(2) Date: Jul. 29, 2014

(87) PCT Pub. No.: WO2013/163034
PCT Pub. Date: Oct. 31, 2013

(65) Prior Publication Data
US 2015/0045820 A1    Feb. 12, 2015

Related U.S. Application Data

(60) Provisional application No. 61/637,611, filed on Apr. 24, 2012.

(51) Int. Cl.
*A61F 9/007* (2006.01)
*A61F 9/013* (2006.01)

(52) U.S. Cl.
CPC ...... *A61F 9/00736* (2013.01); *A61F 9/00781* (2013.01); *A61F 9/0133* (2013.01)

(58) Field of Classification Search
CPC .. A61F 9/007; A61F 9/00736; A61F 9/00754; A61F 9/00781; A61F 9/013;
(Continued)

(56) References Cited

U.S. PATENT DOCUMENTS 2,130,949 A    9/1938   Wharton
3,776,238 A    12/1973  Peyman et al.
(Continued)

FOREIGN PATENT DOCUMENTS

EP    0073803 B1    7/1985
EP    1455698 A1    9/2004
(Continued)

OTHER PUBLICATIONS

Anderson, D. R. (1983) "Trabeculotomy compared to goniotomy for glaucoma in children," *Ophthalmology* 90(7), 805-806.
(Continued)

*Primary Examiner* — Todd J Scherbel
(74) *Attorney, Agent, or Firm* — Morgan, Lewis & Bockius LLP

(57) ABSTRACT

The present invention relates to a microsurgical device and methods of its use for treatment of various conditions including eye diseases, such as glaucoma, using minimally invasive surgical techniques. The invention relates to a dual-blade device for cutting the trabecular meshwork (TM) in the eye. The device tip provides entry into the Schlemm's canal via its size (i.e., for example, 0.3-0.2 mm width) and configuration where the blade tip curves up providing a ramp-like action for cutting the TM. The dimensions and configuration of the blade is such that an entire strip of TM is removed without leaving TM leaflets behind and without causing collateral damage to adjacent tissues.

22 Claims, 24 Drawing Sheets

(58) Field of Classification Search
CPC .............. A61F 9/0133; A61F 9/0136; A61F 2009/00868; A61B 17/3209; A61B 17/32093; A61B 17/3211
See application file for complete search history.

(56) References Cited

U.S. PATENT DOCUMENTS

| | | | |
|---|---|---|---|
| 3,882,872 | A | 5/1975 | Douvas et al. ............... 128/305 |
| 4,011,869 | A | 3/1977 | Seiler, Jr. |
| 4,111,207 | A | 9/1978 | Seiler, Jr. |
| 4,428,748 | A | 1/1984 | Peyman et al. |
| 4,501,274 | A | 2/1985 | Skjaerpe ....................... 606/167 |
| 4,559,942 | A | 12/1985 | Eisenberg |
| 4,577,629 | A | 3/1986 | Martinez |
| 4,649,919 | A | 3/1987 | Thimsen et al. |
| 4,682,597 | A | 7/1987 | Myers |
| 4,900,300 | A | 2/1990 | Lee |
| 5,042,008 | A | 8/1991 | Iwasa et al. |
| 5,163,433 | A | 11/1992 | Kagawa et al. |
| 5,222,959 | A | 6/1993 | Anis |
| 5,224,950 | A | 7/1993 | Prywes |
| 5,431,671 | A | 7/1995 | Nallakrishnan ............... 606/167 |
| 5,478,338 | A | 12/1995 | Reynard |
| 5,487,747 | A | 1/1996 | Stagmann et al. |
| 5,558,637 | A | 9/1996 | Allonen et al. |
| 5,569,283 | A | 10/1996 | Green et al. .................. 606/170 |
| 5,620,453 | A | 4/1997 | Nallakrishnan |
| 5,674,233 | A | 10/1997 | Dybbs |
| 5,713,915 | A * | 2/1998 | Van Heugten ........ A61F 9/0133 606/166 |
| 5,817,115 | A | 10/1998 | Nigam |
| 5,865,831 | A | 2/1999 | Cozean et al. |
| 6,013,049 | A | 1/2000 | Rockley et al. |
| 6,139,559 | A | 10/2000 | Norden et al. |
| 6,213,997 | B1 | 4/2001 | Hood et al. ........................ 606/5 |
| 6,241,721 | B1 | 6/2001 | Cozean et al. |
| 6,251,103 | B1 | 6/2001 | Berlin |
| 6,264,668 | B1 * | 7/2001 | Prywes ................... A61F 9/007 600/567 |
| 6,388,043 | B1 | 5/2002 | Langer et al. .................. 528/80 |
| 6,428,501 | B1 | 8/2002 | Reynard |
| 6,497,712 | B1 | 12/2002 | Feaster ......................... 606/167 |
| 6,503,262 | B1 | 1/2003 | Edens |
| 6,720,402 | B2 | 4/2004 | Langer et al. .................. 528/76 |
| 6,759,481 | B2 | 7/2004 | Tong ............................. 525/241 |
| 6,979,328 | B2 | 12/2005 | Baerveldt et al. .............. 606/41 |
| 7,374,566 | B1 | 5/2008 | Schossau ....................... 606/107 |
| 7,604,663 | B1 | 10/2009 | Reimink et al. ............... 623/2.1 |
| 7,632,303 | B1 | 12/2009 | Stalker et al. ............... 623/1.19 |
| 7,648,591 | B2 | 1/2010 | Furst et al. .................... 148/423 |
| 7,785,321 | B2 | 8/2010 | Baerveldt et al. ................ 606/6 |
| 7,935,131 | B2 | 5/2011 | Anthamatten et al. ........ 606/231 |
| 7,955,387 | B2 | 6/2011 | Richter ....................... 623/11.11 |
| 7,959,641 | B2 | 6/2011 | Sorensen et al. ............. 606/170 |
| 8,038,923 | B2 | 10/2011 | Berger et al. ................. 264/313 |
| 9,757,279 | B2 * | 9/2017 | Kahook ................ A61F 9/0133 |
| 9,872,799 | B2 * | 1/2018 | Kahook ................ A61F 9/0133 |
| 2001/0029386 | A1 | 10/2001 | Matsutani et al. |
| 2002/0026205 | A1 | 2/2002 | Matsutani et al. ............ 606/167 |
| 2002/0111608 | A1 | 8/2002 | Baerveldt et al. ................ 606/6 |
| 2003/0208217 | A1 | 11/2003 | Dan .............................. 606/166 |
| 2005/0070941 | A1 | 3/2005 | Isogimi |
| 2005/0113644 | A1 | 5/2005 | Obenchain et al. |
| 2005/0216019 | A1 | 9/2005 | Eckman |
| 2006/0015128 | A1 | 1/2006 | Fard |
| 2006/0106370 | A1 | 5/2006 | Baerveldt et al. ................ 606/6 |
| 2006/0149194 | A1 | 7/2006 | Conston et al. ............... 606/294 |
| 2006/0241580 | A1 | 10/2006 | Mittelstein et al. .............. 606/4 |
| 2006/0271074 | A1 | 11/2006 | Ewers et al. |
| 2007/0073275 | A1 | 3/2007 | Conston et al. .................. 606/6 |
| 2007/0100363 | A1 | 5/2007 | Dollar et al. |
| 2007/0276420 | A1 | 11/2007 | Sorensen et al. ............. 606/167 |
| 2009/0248141 | A1 | 10/2009 | Shandas et al. .............. 623/1.19 |
| 2009/0287233 | A1 | 11/2009 | Huculak ....................... 606/167 |
| 2009/0306689 | A1 | 12/2009 | Welty et al. |
| 2010/0152609 | A1 | 6/2010 | Zwolinski et al. |
| 2010/0268175 | A1 | 10/2010 | Lunsford et al. |
| 2011/0077626 | A1 | 3/2011 | Baerveldt et al. ................ 606/6 |
| 2011/0202049 | A1 | 8/2011 | Jia et al. |
| 2011/0230877 | A1 | 9/2011 | Huculak et al. ................ 606/41 |
| 2012/0083727 | A1 | 4/2012 | Barnett ........................... 604/22 |
| 2012/0239056 | A1 | 9/2012 | Dijkman et al. |
| 2014/0030273 | A1 | 1/2014 | Verploegen et al. |
| 2014/0121697 | A1 | 5/2014 | Scheller et al. |
| 2016/0354248 | A1 | 12/2016 | Kahook |
| 2017/0181892 | A1 | 6/2017 | Kahook et al. |
| 2017/0367890 | A1 | 12/2017 | Kahook |
| 2018/0133056 | A1 | 5/2018 | Kahook |

FOREIGN PATENT DOCUMENTS

| | | |
|---|---|---|
| EP | 1615604 A1 | 1/2006 |
| EP | 2303203 A1 | 4/2011 |
| KR | 1020040058309 | 9/2004 |
| WO | WO/2011/078631 | 10/2001 |
| WO | WO/2003/045290 | 6/2003 |
| WO | WO/2004/093761 | 11/2004 |
| WO | WO/2004/110501 | 12/2004 |
| WO | WO/2009/140185 | 11/2009 |
| WO | WO/2011/030081 | 3/2011 |
| WO | WO-2012044952 A2 | 4/2012 |
| WO | WO-2012137186 A1 | 10/2012 |
| WO | WO-2013163034 A1 | 10/2013 |
| WO | WO-20017112893 A1 | 6/2017 |

OTHER PUBLICATIONS

Francis, B. A. et al. (2006) "Ab interno trabeculectomy: development of a novel device (Trabectome®) and surgery for open-angle glaucoma," *Journal of Glaucoma* 15(1), 68-73.
Grant, W. (1963) "Experimental aqueous perfusion in enucleated human eyes," *Archives of Ophthalmology* 69(6), 783-801.
Grant, W. M. (1951) "Clinical measurements of aqueous outflow," *A.M.A. Archives of Ophthalmology* 46(2), 113-131.
Herschler, J. et al. (1980) "Modified goniotomy for inflammatory glaucoma. Histologic evidence for the mechanism of pressure reduction," *Archives of Ophthalmology* 98(4), 684-687.
Jacobi, P. C. et al. (1997) "Technique of goniocurettage: a potential treatment for advanced chronic open angle glaucoma," *British Journal of Ophthalmology* 81(4), 302-307.
Jacobi, P. C. et al. (1999) "Goniocurettage for removing trabecular meshwork: clinical results of a new surgical technique in advanced chronic open-angle glaucoma," *American Journal of Ophthalmology* 127(5), 505-510.
Jea, S. Y. et al. (2012) "Ab Interno Trabeculectomy Versus Trabeculectomy for Open-Angle Glaucoma," *Ophthalmology* 119(1), 36-42.
Johnson, D. H. et al. (1987) "Human trabecular meshwork organ culture. A new method," *Investigative Ophthalmology & Visual Science* 28(6), 945-953.
Luntz, M. H. et al. (1977) "Trabeculotomy ab externo and trabeculectomy in congenital and adult-onset glaucoma," *American Journal of Ophthalmology* 83(2), 174-179.
Minckler, D. S. et al. (2005) "Clinical Results with the Trabectome® for Treatment of Open-Angle Glaucoma," *Ophthalmology* 112(6), 962-967.
Pantcheva, M. B. et al. (2010) "Ab Intern Trabeculectomy," *Middle East African Journal of Ophthalmology* 17(4), 287-289.
Quigley, H. A. et al. (2006) "The number of people with glaucoma worldwide in 2010 and 2020," *British Journal of Ophthalmology* 90(3), 262-267.
Seibold, L. K. et al. (2013) "Preclinical Investigation of Ab Interno Trabeculectomy Using a Novel Dual-Blade Device," *American Journal of Ophthalmology* 155(3), 524-529.e522.
Tan, Y. et al. (2011) "Postoperative complications after glaucoma surgery for primary angle-closure glaucoma vs primary open-angle glaucoma," *Archives of Ophthalmology* 129(8), 987-992.
Ting, J. L. M. et al. (2012) "Ab interno trabeculectomy: Outcomes in exfoliation versus primary open-angle glaucoma," *Journal of Cataract & Refractive Surgery* 38(2), 315-323.

(56) References Cited

OTHER PUBLICATIONS

PCT International Search Report of International Application No. PCT/US2013/037374 dated Jul. 25, 2013.
International Search Report and Written Opinion for Application No. PCT/US2016/068393, dated Apr. 17, 2017, 29 pages.
Supplementary European search report, dated Jul. 9, 2015.
International Search Report and Written Opinion for Application No. PCT/US2018/056935, dated Jan. 31, 2019, 12 pages.
European Office Action for Application No. 13781487.7, dated Dec. 20, 2018, 4 pages.

* cited by examiner

MODIFIED DUAL-BLADE CUTTING SYSTEM

CROSS-REFERENCE TO RELATED APPLICATIONS

The present application claims the benefit of U.S. Provisional Patent Application No. 61/637,611, filed on. Apr. 24, 2012, which is incorporated herein by reference [1].

FIELD OF THE INVENTION

This invention is in the field of surgical medicinal intervention. For example, the present invention relates to a microsurgical device and methods of its use for treatment of various medical conditions including but not limited to eye diseases, such as glaucoma, using minimally invasive surgical techniques. Specifically, the device may be a dual-blade device for cutting the trabecular meshwork (TM) in the eye. In particular, the device may have a device tip providing entry into the Schlemm's canal via its size (i.e., for example, between approximately 0.3-0.2 mm width) and a configuration where the entry blade tip curves up providing a ramp-like action for cutting the TM.

BACKGROUND OF THE INVENTION

There are numerous medical and surgical procedures in which it is desirable to cut and remove a strip of tissue of controlled width from the body of a human or veterinary patient. For example, it may sometimes be desirable to form an incision of a controlled width (e.g., an incision that is wider than an incision made by a typical scalpel, cutting blade or needle) in the eye, skin, mucous membrane, tumor, organ or other tissue or a human or animal. In addition, it may sometimes be desirable to remove a strip or quantity of tissue from the body of a human or animal for use as a biopsy specimen, for chemical/biological analysis, for retention or archival of DNA identification purposes, etc. In addition, some surgical procedures require removal of a strip of tissue of a known width from an anatomical location within the body of a patient.

One surgical procedure wherein a strip of tissue of a known width is removed from an anatomical location within the body of a patient is an ophthalmological procedure used to treat glaucoma. This ophthalmological procedure is sometimes referred to as a gonioctomy. In a gonioctomy procedure, a device that is operative to cut or ablate a strip of tissue of approximately 2-10 mm in length or more and about 50-200 μm in width is inserted into the anterior chamber of the eye and used to remove a full thickness strip of tissue from the trabecular meshwork. The trabecular meshwork is a loosely organized, porous network of tissue that overlies a collecting canal known as Schlemm's canal. A fluid, known as aqueous humor, is continually produced in the anterior chamber of the eye. In normal individuals, aqueous humor flows through the trabecular meshwork, into Schlemm's canal and out of the eye through a series of ducts called collector channels. In patients who suffer from glaucoma, the drainage of aqueous humor from the eye may be impaired by elevated flow resistance through the trabecular meshwork, thereby resulting in an Increase in intraocular pressure. The gonioctomy procedure can restore normal drainage of aqueous humor from the eye by removing a full thickness segment of the trabecular meshwork, thus allowing the aqueous humor to drain through the open area from which the strip of trabecular meshwork has been removed. The gonioctomy procedure and certain prior art instruments useable to perform such procedure are described In U.S. patent application Ser. No. 10/052,473 issued as U.S. Pat. No. 6,979,328 (Baerveldt) [2], the entirety of which is expressly incorporated herein by reference.

At present there remains a need in the art for the development of simple, inexpensive and accurate instruments useable to perform the procedure of cutting the trabecular meshwork (TM) in the eye and effectively remove a complete full thickness strip of TM without leaving TM leaflets as well as other procedures where it is desired to remove a strip of tissue from a larger mass of tissue.

SUMMARY OF THE INVENTION

This invention is in the field of surgical medicinal intervention. For example, the present invention relates to a microsurgical device and methods of its use for treatment of various medical conditions including but not limited to eye diseases, such as glaucoma, using minimally invasive surgical techniques. Specifically, the device may be a dual-blade device for cutting the trabecular meshwork (TM) in the eye. In particular, the device may have a device tip providing entry into the Schlemm's canal via its size (i.e., for example, between approximately 0.3-0.2 mm width) and a configuration where the entry blade tip curves up providing a ramp-like action for cutting the TM.

In one embodiment, the invention relates to a device comprising: a handle 1, interface of tool shaft and handle 2, a tool shaft 3, interface of tool shaft and beveled platform 4, beveled platform 5, a first end/beveled platform tip/insertion blade tip 6, a second end/back of the beveled platform 7, a first side 8, a second side 9, a first blade 10, and a second blade 11.

In one embodiment, the invention relates to a device 12 comprising: a handle 1 that necks down to a tool shaft 3 by a first interface 2 wherein said tool shaft widens into a beveled platform 5 by a second interface 4, wherein said beveled platform comprises a insertion blade tip 6 on a distal end of the beveled platform comprising a ramp from said insertion blade tip back towards the posterior end the beveled platform, and a first lateral blade 10 and second lateral blade 11 along the sides of said beveled platform. In one embodiment, said sides of said beveled platform comprise a first side 8 and a second side 9. In one embodiment, said first lateral blade 10 and second lateral blade 11 are in a perpendicular alignment to the bottom of the beveled platform. In one embodiment, the the platform 5 is set at a specific angle and orientation relative to said handle 1. In one embodiment, the platform 5 freely rotates in at least two dimensions. In one embodiment, said handle 1 and beveled platform 5 are operably attached at an angle ranging between 90 and 120 degrees in the Y-Z axis. In one embodiment, said handle 1 and beveled platform 5 are operably attached at an angle ranging between 90 and 180 degrees in the X-Z axis. In one embodiment, said platform 5 freely rotates in an X-Y dimension relative to said handle 1. In one embodiment, said platform 5 remains at a fixed angle in the X-Y, X-Z, and Y-Z dimensions relative to said handle 1. In one embodiment, said platform 5 freely rotates in a positive Z dimension relative to said handle 1. In one embodiment, said beveled platform 5 comprises a first end/beveled platform tip/insertion blade tip 6 and a second end/back of the beveled platform 7, wherein said second end/back of the beveled platform 7 is between 2 and 30 greater in thickness relative to the thickness of said first end/beveled platform tip/insertion blade tip 6. In one embodiment, the dimensions of the beveled platform 5 are calculated using the formula $A^2+B^2=C^2$, wherein A is the length of said beveled platform 5 from said insertion blade tip 6 to the back of the beveled platform 7, B is the height of the beveled platform 5 and C is the length of the ramp formed by the beveled platform insertion blade tip up to the height of said beveled platform. In one embodiment, the height of said beveled platform 5 is not to exceed 0.5 millimeters. In one embodiment, the length of said beveled platform 5 from said insertion blade tip 6 to the back of the beveled platform 7 is not to exceed 1.0 millimeters. In one embodiment, the width of said beveled platform 5 is not to exceed 0.35 millimeters. In one embodiment, said beveled platform 5 increases in thickness from a fine blade tip towards the second end/back of the beveled platform 7 in the direction of the Y-axis. In one embodiment, said first end/beveled platform tip/insertion blade tip 6 comprises a pointed tip with fine edges of surgical sharpness. In one embodiment, said first end/beveled platform tip/insertion blade tip 6 comprises a lancet. In one embodiment, said beveled platform 5 further comprises a first blade 10 and a second blade 11. In one embodiment, said first blade 10 is attached to a first side 8 of said second end/back of the beveled platform 7. In one embodiment, said first blade 10 and beveled platform 5 are operably attached at an angle ranging between 90 and 180 degrees in the Y-Z axis. In one embodiment, said angle is preferably between 90 and 120 degrees in the Y-Z axis. In one embodiment, said second blade 11 and beveled platform 5 are operably attached at an angle ranging between 90 and 120 degrees in the Y-Z axis. In one embodiment, said first blade 10 and handle 1 are operably positioned at an angle ranging between 90 and 120 degrees in the Y-Z axis. In one embodiment, said second blade 11 and handle 1 are operably positioned at an angle ranging between 90 and 120 degrees in the Y-Z axis. In one embodiment, said second blade 11 is attached to a second side 9 of said second end/back of the beveled platform 7. In one embodiment, said beveled platform 5 increases in thickness from said second side 9 towards the first side 8 in the direction of the X-axis. In one embodiment, said beveled platform 5 increases in thickness from said first side 8 towards the second side 9 in the direction of the X-axis. In one embodiment, said beveled platform 5 increases in thickness from said second side 9 towards the first side 8 in the direction of the X-axis and said beveled platform 5 increases in thickness from a fine blade tip of the first end 6 towards the second end/back of the beveled platform 7 in the direction of the Y-axis. In one embodiment, said beveled platform 5 increases in thickness from said first side 8 towards the second side 9 in the direction of the X-axis and said beveled platform 5 increases in thickness from a fine blade tip of the first end 6 towards the second end/back of the beveled platform 7 in the direction of the Y-axis. In one embodiment, said first blade 10 and said second blade 11 are parallel. In one embodiment, said first blade 10 and said second blade 11 extend above the top surface of said second end/back of the beveled platform 7. In one embodiment, said first blade 10 and said second blade 11 are positioned at an angle between approximately 100 to 140 degrees relative to the top surface of said second end/back of the beveled platform 7. In one embodiment, said beveled platform 5 is approximately 0.3 millimeters wide. In one embodiment, said beveled platform 5 is approximately 0.2 millimeters wide. In a preferred embodiment, said beveled platform 5 is approximately 0.25 millimeters wide.

In one embodiment, the invention relates to a device comprising a handle and a beveled platform, wherein said platform freely rotates in at least two dimensions. In one embodiment, said handle and beveled platform are operably attached at an angle ranging between 90 and 120 degrees. In one embodiment, said platform freely rotates in an X-Y dimension relative to said handle. In one embodiment, said platform freely rotates in a positive Z dimension relative to said handle. In one embodiment, said beveled platform comprises a first end and a second end, wherein said second end is at least 20 times greater in thickness relative to said first end. In one embodiment, said beveled platform further comprises a first blade and a second blade. In one embodiment, said first blade is attached to a first side of said second end. In one embodiment, said second blade is attached to a second side of said second end. In one embodiment, said first blade and said second blade are parallel. In one embodiment, said first blade and said second blade extend above the top surface of said second end. In one embodiment, said first lateral blade and said second lateral blade are positioned at an angle between approximately 100-140 degrees in the Y-Z axis relative to the bottom surface of said beveled platform. In one embodiment, said beveled platform is approximately 0.3 millimeters wide. In one embodiment, said beveled platform 5 is approximately 0.2 millimeters wide. In a preferred embodiment, said beveled platform 5 is approximately 0.25 millimeters wide.

In one embodiment, said beveled platform is set at a specific angle and orientation relative to said handle. In one embodiment, said handle and beveled platform are operably attached at an angle ranging between 90 and 120 degrees in the Y-Z axis. In one embodiment, said handle and beveled platform are operably attached at an angle ranging between 90 and 180 degrees in the X-Z axis. In one embodiment, said platform freely rotates in an X-Y dimension relative to said handle. In one embodiment, said platform remains at a fixed angle in the X-Y, X-Z, and Y-Z dimensions relative to said handle. In one embodiment, said platform freely rotates in a positive Z dimension relative to said handle. In one embodiment, the dimensions of the beveled platform are calculated by the formula $A^2+B^2=C^2$, wherein A is the length of said beveled platform from said beveled platform insertion blade tip to the posterior end of the beveled platform, B is the height of the beveled platform and C is the length of the ramp formed by the beveled platform insertion blade tip up to the height of said beveled platform. In one embodiment, the height of said beveled platform is not to exceed 0.5 millimeters. In one embodiment, the length of said beveled platform from said beveled platform insertion blade tip to the posterior end of the beveled platform is not to exceed 1.0 millimeters. In one embodiment, the height of said beveled platform is greater than 0.5 millimeters. In one embodiment, the length of said beveled platform from said beveled platform insertion blade tip to the posterior end of the beveled platform is greater than 1.0 millimeters. In one embodiment, the width of said beveled platform 5 is not to exceed 0.35 millimeters. In one embodiment, said beveled platform 5 is approximately 0.2 millimeters wide. In a preferred embodiment, said beveled platform 5 is approximately 0.25 millimeters wide. In one embodiment, said beveled platform increases in thickness from a fine blade tip towards the posterior end of the beveled platform in the direction of the Y-axis. In one embodiment, said beveled platform insertion blade tip comprises a pointed tip with fine edges of surgical sharpness. In one embodiment, said beveled platform insertion blade tip comprises a lancet. In one embodiment, said beveled platform further comprises a first lateral blade and a second lateral blade. In one embodiment, said first lateral blade is attached to a first side of said posterior end of the beveled platform. In one embodiment, said first lateral blade and beveled platform are operably attached at an angle ranging between 90 and 180 degrees in the Y-Z axis. In one embodiment, said angle is preferably between 90 and 120 degrees in the Y-Z axis. In one embodiment, said second blade and beveled platform are operably attached at an angle ranging between 90 and 120 degrees in the Y-Z axis. In one embodiment, said first lateral blade and handle are operably positioned at an angle ranging between 90 and 120 degrees in the Y-Z axis. In one embodiment, said second lateral blade and handle are operably positioned at an angle ranging between 90 and 120 degrees in the Y-Z axis. In one embodiment, said second lateral blade is attached to a second side 9 of said posterior end of the beveled platform. In one embodiment, said beveled platform increases in thickness from said second side towards the first side in the direction of the X-axis. In one embodiment, said beveled platform increases in thickness from said first side towards the second side in the direction of the X-axis. In one embodiment, said beveled platform increases in thickness from said second side towards the first side in the direction of the X-axis and said beveled platform increases in thickness from a fine blade tip of the beveled platform insertion blade tip towards the posterior end of the beveled platform in the direction of the Y-axis. In one embodiment, said beveled platform increases in thickness from said first side towards the second side in the direction of the X-axis and said beveled platform increases in thickness from a fine blade tip of the beveled platform insertion blade tip towards the posterior end of the beveled platform in the direction of the Y-axis. In one embodiment, said first lateral blade and said second lateral blade are parallel. In one embodiment, said first lateral blade and said second lateral blade extend above the top surface of said posterior end of the beveled platform. In one embodiment, said first lateral blade and said second lateral blade are positioned at an angle between approximately 100 to 140 degrees in the Y-Z axis relative to the bottom surface of said posterior end of the beveled platform. In one embodiment, said beveled platform is approximately 0.3 millimeters wide. In one embodiment, said beveled platform 5 is approximately 0.2 millimeters wide. In a preferred embodiment, said beveled platform 5 is approximately 0.25 millimeters wide. In one embodiment, said device is integrated into an endoscope. In one embodiment, said device is placed on the end of the endoscope. In one embodiment, said device is made from at least one of the following materials: titanium, stainless steel, polyether ether ketone, shape memory alloy, and shape memory polymers. In one embodiment, said device is rigid at room temperature, but is more flexible at body temperature. In one embodiment, portions of the device of the current invention are rigid at room temperature, but are more flexible at body temperature. In one embodiment, portions of the device are made from different materials. In one embodiment, portions of the device are made from materials of various rigidity. In one embodiment, said tool shaft is flexible. In one embodiment, said tool shaft is made from a lower density material.

In one embodiment, the invention relate to a method for cutting a strip of tissue of width W from a tissue mass, said method comprising the steps of: a) providing a device which comprises; i) a handle attached to a beveled platform, ii) an anterior insertion blade tip of the beveled platform expanding backwards to a posterior end of the beveled platform, iii) a first side of the beveled platform upon which is affixed a first lateral blade, iv) a second side of the beveled platform upon which is affixed a second lateral blade; v) at least first and second lateral cutting edges formed by blades in a generally perpendicular and posterior position to said opposite edges of said anterior insertion blade tip of the beveled platform, said first and second cutting edges being separated by a distance D that is approximately equal to the width W of the strip of tissue to be cut; b) advancing the anterior insertion blade tip of the beveled platform through tissue such that the first and second cutting edges are positioned adjacent to tissue to be cut; c) advancing the distal end such that the cutting edges cut a strip of tissue of approximate width W and the cut strip of tissue remains substantially intact. In one embodiment, the mass of tissue is in vivo. In one embodiment, the mass of tissue is in vitro. In one embodiment, said device is integrated into an endoscope. In one embodiment, said cutting is under direct visualization. In one embodiment, the mass of tissue is located within the body of a human or animal subject. In one embodiment, the strip of tissue is removed for a diagnostic or therapeutic purpose. In one embodiment, the subject suffers from glaucoma and wherein the method is carried out to remove a strip of trabecular meshwork from an eye of the subject to facilitate drainage of aqueous humor from the eye thereby lowering intraocular pressure. In one embodiment, said eye has a dilated pupil. In one embodiment, step b comprises inserting the device into the anterior chamber of the eye; positioning the anterior insertion blade tip of the beveled platform adjacent to or within the trabecular meshwork of the eye; and advancing the cutting tube such that the cutting edges cut a strip of approximate width W from the trabecular meshwork. In one embodiment, the device provided in step a of the method further comprises an anterior insertion blade tip of the beveled platform and wherein the anterior insertion blade tip of the beveled platform is advanced through the trabecular meshwork and into Schlemm's canal and, thereafter, the anterior insertion blade tip of the beveled platform is advanced through Schlemm's canal as the cutting tube is advanced to cut the strip of tissue. In one embodiment, the device provided in step a further comprises apparatus for severing the strip of tissue after the strip of tissue has reached a desired length and wherein the method further comprises the step of: severing the strip of tissue after the strip of tissue has reached a desired length. In one embodiment, the method is carried out to form an incision in skin, mucous membrane, an organ, a tumor or other anatomical structure. In one embodiment, the method further comprises the step of: c) removing the entire strip of tissue.

In one embodiment, the invention relates to a method for cutting a strip of tissue of width W from a tissue mass, said method comprising the steps of: a) providing a device which comprises; i) a handle attached to a beveled platform, ii) an anterior insertion blade tip of the beveled platform expanding backwards to a posterior end of the beveled platform, iii) a first side of the beveled platform upon which is affixed a first lateral blade, iv) a second side of the beveled platform upon which is affixed a second lateral blade; v) at least first and second lateral cutting edges formed by blades in a generally perpendicular and posterior position to said opposite edges of said anterior insertion blade tip of the beveled platform, said first and second cutting edges being separated by a distance D that is approximately equal to the width W of the strip of tissue to be cut; b) advancing the anterior insertion blade tip of the beveled platform through tissue such that the first and second cutting edges are positioned adjacent to tissue to be cut; c) advancing the distal end such that the cutting edges cut a strip of tissue of approximate width W and the cut strip of tissue remains substantially intact. In one embodiment, the mass of tissue is in vivo. In one embodiment, the mass of tissue is in vitro. In one embodiment, the mass of tissue is located within the body of a human or animal subject. In one embodiment, the strip of tissue is removed for a diagnostic or therapeutic purpose. In one embodiment, the subject suffers from glaucoma and wherein the method is carried out to remove a strip of trabecular meshwork from an eye of the subject to facilitate drainage of aqueous humor from the eye thereby lowering intraocular pressure. In one embodiment, step b comprises inserting the device into the anterior chamber of the eye; positioning the anterior insertion blade tip of the beveled platform adjacent to or within the trabecular meshwork of the eye; and advancing the cutting tube such that the cutting edges cut a strip of approximate width W from the trabecular meshwork. In one embodiment, the device provided in step a of the method further comprises an anterior insertion blade tip of the beveled platform and wherein the anterior insertion blade tip of the beveled platform is advanced through the trabecular meshwork and into Schlemm's canal and, thereafter, the anterior insertion blade tip of the beveled platform is advanced through Schlemm's canal as the cutting tube is advanced to cut the strip of tissue. In one embodiment, the device provided in step a further comprises apparatus for severing the strip of tissue after the strip of tissue has reached a desired length and wherein the method further comprises the step of severing the strip of tissue after the strip of tissue has reached a desired length. In one embodiment, the method is carried out to form an incision in skin, mucous membrane, an organ, a tumor or other anatomical structure. In one embodiment, the method is carried out to remove tissue from the vascular system. In one embodiment, the method is carried out to remove tissue from the lymphatic system. In one embodiment, the invention further comprises the step of: c) removing the strip of tissue.

It is not intended that embodiments of the invention be limited to any particular method, medical target, or device confirmation; however, it is believed that the device may be optimally designed to remove trabecular meshwork of the eye, unroofing small vessels (such as veins, arteries, lymphatic vessels, or other vessel with a lumen), and for creating a hole or opening in the tympanic membrane of the ear. It is not intended that embodiments of the invention be limited to any particular mechanism; however, it is believed that creating an opening in the tympanic membrane of the ear may help aid in treating ear disease.

It is not intended that embodiments of the invention be limited to any particular endoscope, it is believed that the device may be optimally designed for an ophthalmic endoscopy system endoscope. One such system is commercially called "Endo Optiks."

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "therapeutically effective amounts" or "pharmaceutically effective amounts", as used herein means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein "goniotomy" refers to a surgical procedure primarily used to treat congenital glaucoma or other types of glaucoma.

As used herein "trabecular meshwork" refers to area of tissue in the eye located around the base of the cornea, near the ciliary body, (between the scleral spur and schwalbe's line) and is responsible for draining the aqueous humor from the eye via the anterior chamber (the chamber on the front of the eye covered by the cornea). The tissue is spongy and lined by trabeculocytes; it allows fluid to drain into a set of tubes called Schlemm's canal and eventually flowing into the blood system.

As used herein "Schlemm's canal" refers to a circular channel in the eye that collects aqueous humor from the anterior chamber and delivers it into the bloodstream via the collector channels and anterior ciliary veins.

As used herein "eye diseases" refers to various conditions of the eye including, but not limited to Glaucoma—optic neuropathy, Glaucoma suspect—ocular hypertension, Primary open-angle glaucoma, Primary angle-closure glaucoma, primary open angle glaucoma, normal or low tension glaucoma, pseudoexfoliation glaucoma, pigment dispersion glaucoma, angle closure glaucoma (acute, subacute, chronic), neovascular or inflammatory glaucoma, ocular hypertension, and other types of glaucoma that are related to dysregulation of intraocular pressure As used herein "hypotony" refers to reduced intraocular pressure. The statistical definition of hypotony is intraocular pressure (TOP) less than 6.5 mmHg, which is more than 3 standard deviations below the mean IOP. The clinical definition of hypotony is IOP low enough to result in pathology (vision loss). The vision loss from low IOP may be caused by corneal edema, astigmatism, cystoid macular edema, maculopathy, or other condition. Hypotony maculopathy is characterized by a low IOP associated with fundus abnormalities, including chorioretinal folds, optic nerve head edema in the acute setting, and vascular tortuosity.

As used herein "Schwalbe's line" refers to the anatomical line found on the interior surface of the eye's cornea, and delineates the outer limit of the corneal endothelium layer. Specifically, it represents the termination of Descemet's membrane.

As used herein "descemet's membrane" refers to the basement membrane that lies between the corneal proper substance, also called stroma, and the endothelial layer of the cornea.

As used herein "scleral spur" refers to an annular structure composed of collagen in the human eye, a protrusion of the sclera into the anterior chamber. It is the origin of the longitudinal fibres of the ciliary muscle and is attached anteriorly to the trabecular meshwork. Open-angle glaucoma (OAG) and closed-angle glaucoma (CAG) may be treated by muscarinic receptor agonists (e.g., pilocarpine), which cause rapid miosis and contraction of the ciliary muscles, this pulls the scleral spur and results in the trabecular meshwork being stretched and separated. This opens the fluid pathways and facilitates drainage of the aqueous humour into the canal of Schlemm and ultimately decreasing intraocular pressure.

As used herein "Trabectome®" refers to a minimally invasive glaucoma surgical tool for the surgical management of adult, juvenile and infantile glaucoma. Unlike a trabeculectomy, the surgery with a Trabectome® should not create an external filtering bleb or require leaving a permanent hole in the eye. Instead, the Trabectome® electosurgical handpiece opens access to the eyes natural drainage system. This procedure is performed through a small incision similar to that of cataract surgery and allows the patient to go home on the same day.

BRIEF DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 20 shows damage to sclera below Schlemm's canal by the blade.

FIG. 21 shows thermal damage to the TM. For the Trabectome® procedure (designed to replace goniotomy and to improve upon that procedure by removing sections of trabecular meshwork) a Trabectome® device was used to engage the trabecular meshwork and cautery was applied to the trabecular meshwork. The circle shows an area where a small segment of trabecular meshwork was removed; however, there are large leaflets of trabecular meshwork remaining and charred tissue on either side of the treatment area. In this previous methodology, the device "burns" tissue and the burning of tissue creates inflammation that leads to more scar formation that leads to failure of the surgically induced opening into Schlemm's canal. In addition, due to cautery, many bubbles are formed during this procedure, which makes visualization difficult during the actual procedure. These issues do not occur with device of the current invention. A representative photo of the Trabectome® is in FIG. 21

FIG. 22 shows no damage to structures adjacent to the normal location of TM. FIG. 22 shows complete removal of TM tissue with no remaining leaflets of TM.

DESCRIPTION OF THE INVENTION

Figure 1:
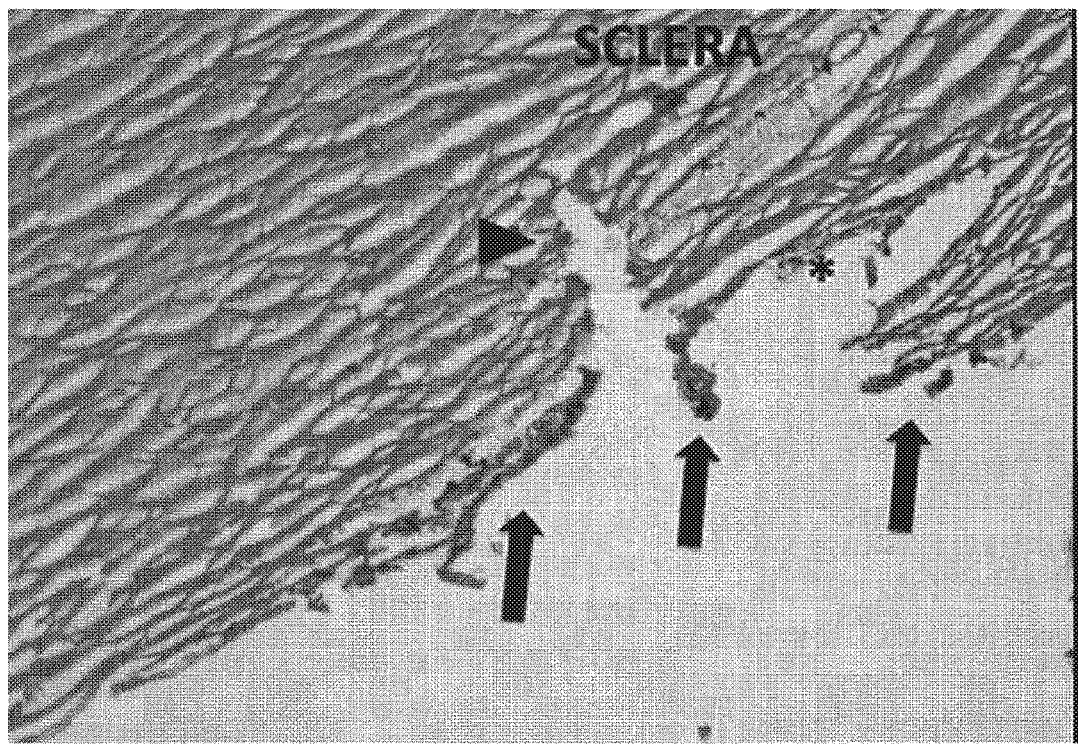
FIG. 1 shows a representative histologic specimen of human anterior chamber angle structures following incision with a microvitreoretinal (MVR) blade. The incision extends through full-thickness trabecular meshwork and the Schlemm's canal and into adjacent sclera (black arrow head). A large portion of trabecular meshwork remains on either side of the incision (black arrows). An asterisk labels the Schlemm's canal. Light micrograph, hematoxylin-eosin, magnification ×100.

Glaucoma is believed to be one of the leading causes of blindness worldwide [7]. It has been reported that a modifiable disease risk factor is intraocular pressure (TOP). Conventional treatment has centered on lowering IOP pharmaceutically with hypotensive medications or surgically through the use of lasers or incisional procedures. The main area of obstruction to aqueous outflow, with subsequent dysregulation of IOP, is thought to be located at the juxtacanalicular trabecular meshwork (TM) and distal outflow structures [8-10]. Performing a goniotomy or trabeculotomy in adults with glaucoma has not been associated with great success in lowering IOP [11, 12]. In contrast, these procedures have been reported to be more successful in congenital glaucoma, where a membrane covering the TM is thought to be a major factor in impedance of aqueous outflow [13]. More recently, there have been attempts to use novel ab interno trabeculectomy procedures to remove TM in adult patients and results have been mixed [14-16].

One reason for poor long-term outcomes with this approach in adults might be related to incomplete removal of TM and membrane formation across the remaining TM leaflets with subsequent elevation in IOP [17]. It is unclear how a more complete removal of TM tissue might compare to procedures that simply incise TM, such as goniotomy, or procedures that cauterize TM with tissue removal, such as Trabectome® (Neomedix, Tustin, Calif., USA). The dual-blade device is specifically designed to conform to the drainage angle anatomy of the human eye. While not limiting the current invention, the device is meant to perform an ab interno trabeculectomy by engaging TM and cutting the target tissue while minimizing leaflets left in place and damage to adjacent tissues. The device was designed and manufactured at the University of Colorado Eye Center (U.S. Provisional Patent Application No. 61/637,611) [1]. Tissue effects from the novel device are compared to those from a goniotomy using a microvitreoretinal (MVR) blade (BD, Franklin Lakes, N.J., USA) and cautery of TM with the Trabectome® device. Human eye perfusion studies were also completed to assess the IOP-lowering efficacy of each approach.

Recently, there has been a growing trend toward innovations in minimally invasive glaucoma surgery (MIGS). The risks and imperfections of guarded filtration surgery and tube shunt procedures have driven this paradigm shift despite the proven long-term efficacy of these incisional procedures. Drawbacks of traditional incisional procedures include unpredictable IOP-lowering results, prolonged visual recovery, long-term risk of infection and vision loss, frequency of follow-up visits, and long-term failure rate [18]. Procedures such as endoscopic cyclophotocoagulation, ab interno trabeculectomy with Trabectome®, and canaloplasty with the iScience illuminated catheter (iScience, Menlo Park, Calif., USA) were all introduced to address limitations of full-thickness surgery, most notably to eliminate the presence of a filtering bleb. However, a major drawback of all of these procedures is the additional equipment cost required and, in some cases, a steep learning curve. The added equipment cost in particular presents a significant hurdle to providers, hospitals, and surgery centers that may require several procedures to recoup the initial investment. Providers and patients may also face opposition from insurance companies regarding coverage of a novel procedure lacking longterm efficacy data. The requirement for additional equipment also limits patient access to these procedures in underserved areas of the world.

Experimental Methods and Results

Approval for a preclinical study [19] was obtained from the Colorado Multiple Institutional Review Board for the use of human material prior to initiation of the study and the tenets of the Declaration of Helsinki were followed. Informed consent was obtained from donors or relatives for use in research by the eye bank from which human globes were obtained.

For histologic analyses, 6 corneal rim specimens were obtained from the Rocky Mountain Lions Eye Bank (Aurora, Colo., USA) and the San Diego Eye Bank (San Diego, Calif., USA). Tissue samples were removed from the storage medium and mounted on a platform with the TM side facing up and secured in place using tissue pins. A total of 2 samples were used for each of the 3 treatment methods studied. An MVR blade was used to incise the central TM under microscopic visualization along the length of 2 corneal rims. For the Trabectome® device, the foot plate of the device tip was inserted into the Schlemm's canal under microscopic visualization. Once in place, the foot pedal was used to apply continuous ablation while advancing the tip slowly across the extent of the TM sample. A standard power setting of 0.8 W was used during treatment. The dual-blade device was used to incise the TM of 2 samples. The blade tip was used to incise TM in a manner similar to that used for goniotomy and the blade was then advanced in a clockwise fashion along the extent of the TM. At the distal end, the blade tip was tilted upwards to incise a complete ribbon of TM and the process was repeated in a counterclockwise fashion to incise the remaining TM tissue.

All tissue samples were then immediately preserved in 4% paraformaldehyde/phosphate-buffered saline overnight at 4° C. and then radially cut into quadrants. Rim sections were processed for histology and embedded into paraffin so that the cut edge of the tissue was facing the front of the block. Tissue sections (6 mm thick) were cut and stained with Mayer's hematoxylin-eosin Y (Richard-Allan Scientific, Kalamazoo, Mich., USA). Bright-field imaging was performed using a Nikon Eclipse 80i microscope (Nikon, Melville, N.Y., USA) equipped with a Nikon D5-Fi1 color camera and a Nikon CFI 103/Plan Fluor objective lens.

Human eye perfusion Studies: A total of 12 human globes from pseudophakic donors with no history of glaucoma were obtained from various eye banks around the country for perfusion studies on each device. The perfusion system used a standard programmable syringe pump (Pump 11 Plus; Harvard Apparatus, Holliston, Mass., USA). Pressure was monitored via an in-line real-time pressure transducer (Research Grade Pressure Transducer; Harvard Apparatus) connected to a single-channel chart recorder (Pharmacia REC-481; Pharmacia/Pfizer New York, N.Y., USA). Polyethylene tubing with a 1.14 mm inner diameter (PE-160; Warner Instruments, Hamden, Conn., USA) was used for all connections.

In each case, the human globe was first prepared by injecting Dulbecco's modified Eagle medium (DMEM; Invitrogen/Life Technologies, Carlsbad, Calif., USA) through the optic nerve with a 26-gauge needle until the globe had returned to a spherical shape. The perfusion line (terminating in another 26-gauge needle) was inserted diagonally through the anterior chamber of the eye, passing through the cornea and pupil and ending with the tip beneath the iris. The globe was surrounded by damp gauze and the perfusion pump (filled with DMEM) was set to an initial inflow rate of 7 mL/min. IOP was allowed to increase until it reached 30 mm Hg. The infusion rate was then reduced to 2-5 mL/min to maintain a steady-state IOP for at least 60 minutes prior to TM incision. A preoperative IOP was measured immediately prior to incision in each case. A 1.7 mm stainless steel keratome blade (BD) was used create a tri-beveled clear corneal incision near the limbus, and the anterior chamber was filled with enough viscoelastic (HealonGV; Abbott Medical Optics, Abbott Park, Ill., USA) to maintain the anterior chamber and provide adequate visualization during the procedure in each case. Each technique was performed under gonioscopic view using a standard direct gonioscope with microscope assistance. The surgical procedure used for each device is described above. In each case, approximately 100-180 degrees of TM was treated. For each device, treatment was started 180 degrees away from the corneal wound and extended along the angle in a clockwise direction. The device was then extended in a counterclockwise direction from the same starting point. Every effort was made to treat the maximum amount of degrees possible with each device. In the case of the dual-blade device and Trabectome®, the instrument was rotated 180 degrees after the initial pass to direct the device tip in the direction of treatment. IOP was allowed to reach a steady state before measuring the postprocedure IOP. Each of the 3 studied surgical techniques was performed on a total of 4 eyes.

Data Analysis

The mean and standard deviation of preprocedure and postprocedure IOP was calculated for each device as well as percent change in IOP. Student paired t tests were used to compare preprocedure and postprocedure IOP for each device. A calculated P value <0.05 was considered to be statistically significant.

Results

Figure 2:
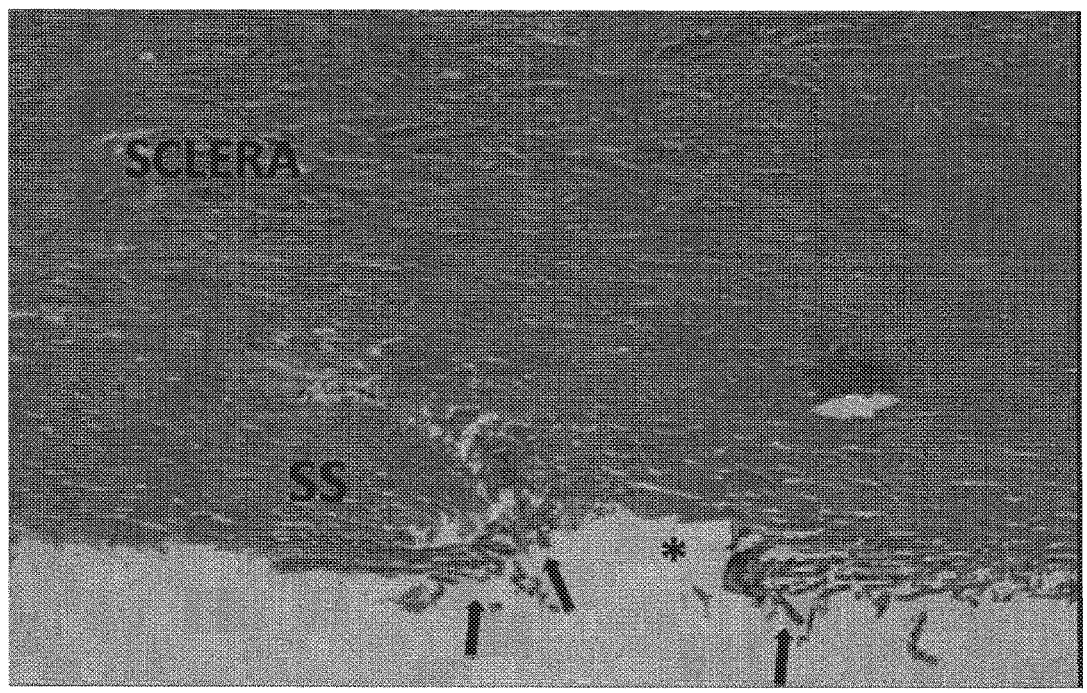
FIG. 2 shows a representative histologic specimen of human anterior chamber angle structures following incision with a Trabectome®. The incision extends through the full-thickness of a trabecular meshwork without damage to adjacent sclera. A portion of trabecular meshwork has been removed centrally with a moderate amount of residual tissue on either side of the incision (black arrows). Charring of the incision edges is noted. An asterisk labels the Schlemm's canal. SS=scleral spur. Light micrograph, hematoxylin eosin, magnification ×100.
Figure 3:
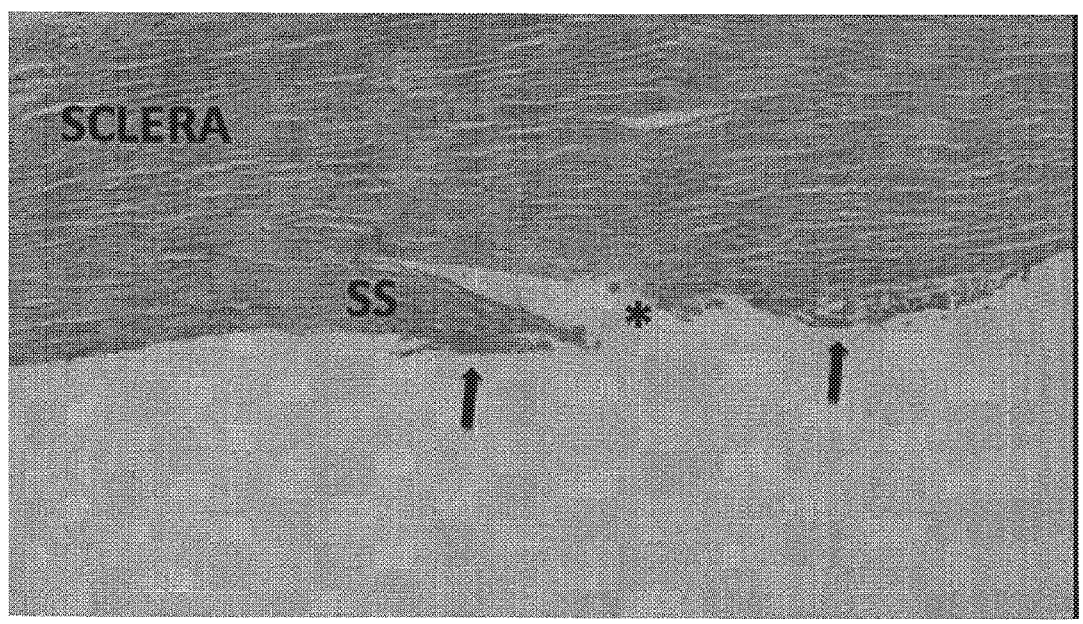
FIG. 3 shows a representative histologic specimen of human anterior chamber angle structures following an incision with a dual blade device. The incision extends through the full-thickness of a trabecular meshwork without injury to adjacent sclera. A near-complete removal of trabecular meshwork tissue has been accomplished (black arrows). An asterisk labels the Schlemm's canal. SS=scleral spur. Light micrograph, hematoxylin-eosin, magnification ×100.

Two corneal rim sections were analyzed for each device. Six-micron-thick histologic sections were taken from various clock hours treated with each device and stained with Mayer's hematoxylin-eosin Y (Richard-Allan Scientific). Findings were consistent across all sections from each device tested. Cuts with the MVR blade exhibited complete incision through the entire thickness of TM tissue. However, there was minimal removal of TM with large leaflets of tissue remaining over the Schlemm's canal. The incision extended deeply through the Schlemm's canal with obvious injury to the adjacent deep sclera in the majority of sections (FIG. 1). The Trabectome® also achieved an opening through the entirety of TM tissue into the Schlemm's canal. Although the device also removed a large portion of the central TM, significant leaflets of residual tissue still remained. The residual TM demonstrated extensive charring from thermal injury. Tissue debris was also noted to be occluding distal collector channels (FIG. 2). Tissue incised with the dual-blade device demonstrated a more complete removal of TM without collateral damage (FIG. 3).

Data from human eye perfusion studies are included in Table 1. The extent of TM treatment varied between devices and between eyes from 100 to 180 degrees. All 3 treatment modalities achieved a significant reduction in measured IOP 30 minutes after treatment. Treatment with the dual-blade device and Trabectome® resulted in a mean IOP reduction of 40% each, whereas the MVR blade achieved a 31% reduction. Although the percentage of IOP decrease was greater for Trabectome® and the dual-blade device, there was no statistically significant difference in the IOP lowering between devices (dualblade/MVR P=0.13; dual-blade/Trabectome® P=0.96; Trabectome®/MVR P=0.12). There was no correlation between the number of degrees of TM treated and the percentage IOP change for any device ($r^2$=0.077-0.271).

TABLE 1

Human Eye Perfusion Studies After Treatment of Trabecular Meshwork by Various Devices

|  | Eye | Degrees of Angle Treated | Preprocedure IOP | Postprocedure IOP | Absolute IOP Change | Percent IOP Change | P Value |
|---|---|---|---|---|---|---|---|
| Dual-blade device | 1 | 140 | 17 | 10 | −7 | −41 |  |
|  | 2 | 180 | 19 | 11 | −8 | −42 |  |
|  | 3 | 130 | 15 | 9 | −6 | −40 |  |
|  | 4 | 180 | 22 | 14 | −8 | −36 |  |
|  | Mean | 157.5 ± 26.3 | 18.3 ± 3.0 | 11.0 ± 2.2 | −7.3 | −40 | 0.00063 |
| MVR blade | 1 | 180 | 20 | 14 | −6 | −30 |  |
|  | 2 | 180 | 20 | 15 | −5 | −25 |  |
|  | 3 | 150 | 18 | 12 | −6 | −33 |  |
|  | 4 | 170 | 16 | 10 | −6 | −38 |  |
|  | Mean | 170.0 ± 14.1 | 18.5 ± 1.9 | 12.8 ± 2.2 | −5.8 | −31 | 0.00018 |
| Trabectome ® | 1 | 120 | 18 | 12 | −6 | −33 |  |
|  | 2 | 130 | 21 | 12 | −9 | −43 |  |
|  | 3 | 100 | 17 | 11 | −6 | −35 |  |
|  | 4 | 120 | 19 | 10 | −9 | −47 |  |
|  | Mean | 117.5 ± 12.6 | 18.8 ± 1.7 | 11.3 ± 1.0 | −7.5 | −40 | 0.00324 |

IOP = intraocular pressure; MVR = microvitreoretinal.

In the study, the initial preclinical evaluation of an embodiment of the present invention, a dual-blade device for the treatment of glaucoma, is presented [19]. Histologic analysis of human cadaver eye tissue treated with the dual-blade device achieved more complete removal of TM tissue while avoiding any discernible damage to surrounding tissue. Treatment with other methods of TM removal such as MVR blade goniotomy and ab interno trabeculectomy with the Trabectome® device failed to attain equivalent histologic results to the novel dual-blade device. While histology data were obtained from ex vivo-treated corneal rims, similar findings were noted when treatment was performed using the ab interno approach on perfused eyes. The near-absence of TM leaflets with the dual-blade device may be beneficial in reducing the chances of future physical obstruction, and the lack of tissue damage may also reduce the inflammatory response or subsequent fibrosis at the surgical site.

In addition to potentially favorable histologic outcomes, the dual-blade device resulted in significant IOP lowering in a human eye perfusion model. Although all 3 devices yielded similar immediate reduction in IOP after use in a perfusion model, it is unclear how a more complete removal of TM tissue and decreased collateral damage with the dual-blade device of the present invention will translate into long term surgical outcomes when used to treat glaucoma. No correlation was found between degrees of TM treated and IOP reduction. It is plausible that IOP reduction may depend more on the number of downstream collector channels exposed rather than the absolute amount of TM removal alone.

Figure 4:
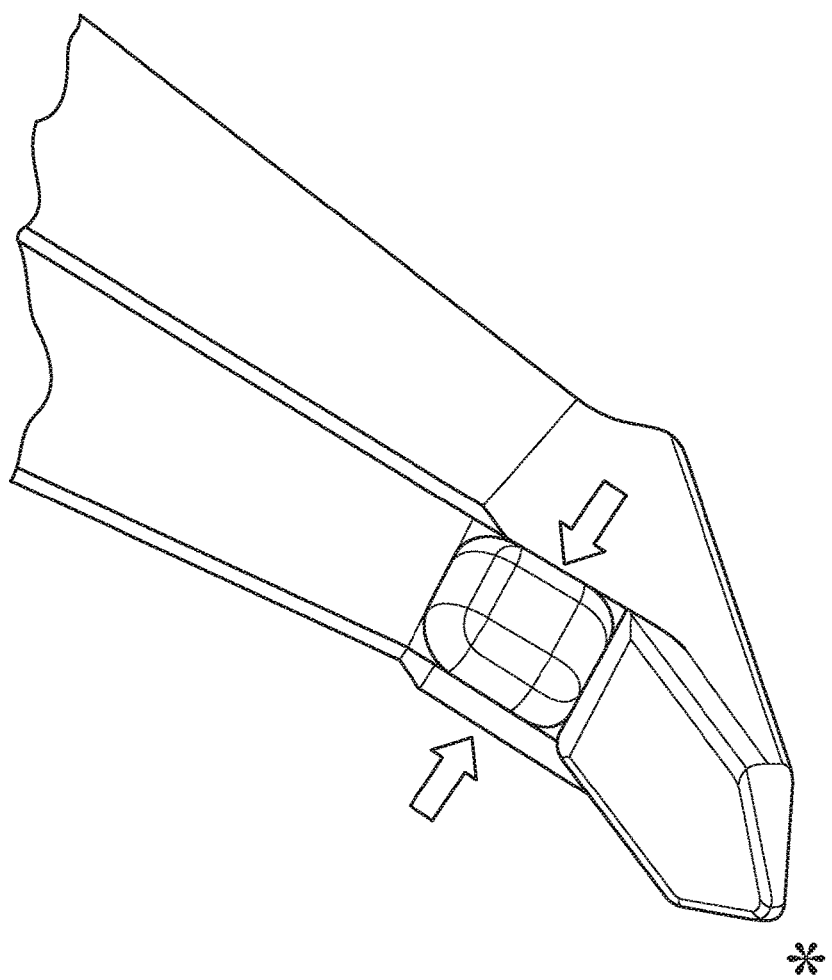
FIG. 4 shows one embodiment of the dual blade device for treatment of glaucoma. The device is illustrated to reveal the dual cutting blades (black arrows) as well as the distal point (asterisk) that is designed to pierce the trabecular meshwork (TM) and enter into the Schlemm's canal. Once in the canal, the device is advanced so that the TM moves up the ramp from the distal point toward the dual cutting blades, which then cleanly incise the presented TM. The distance between the dual blades is designed to closely match that of the width of the TM. The inset is a photo of the first prototype device that was made of medical-grade stainless steel.
Figure 5:
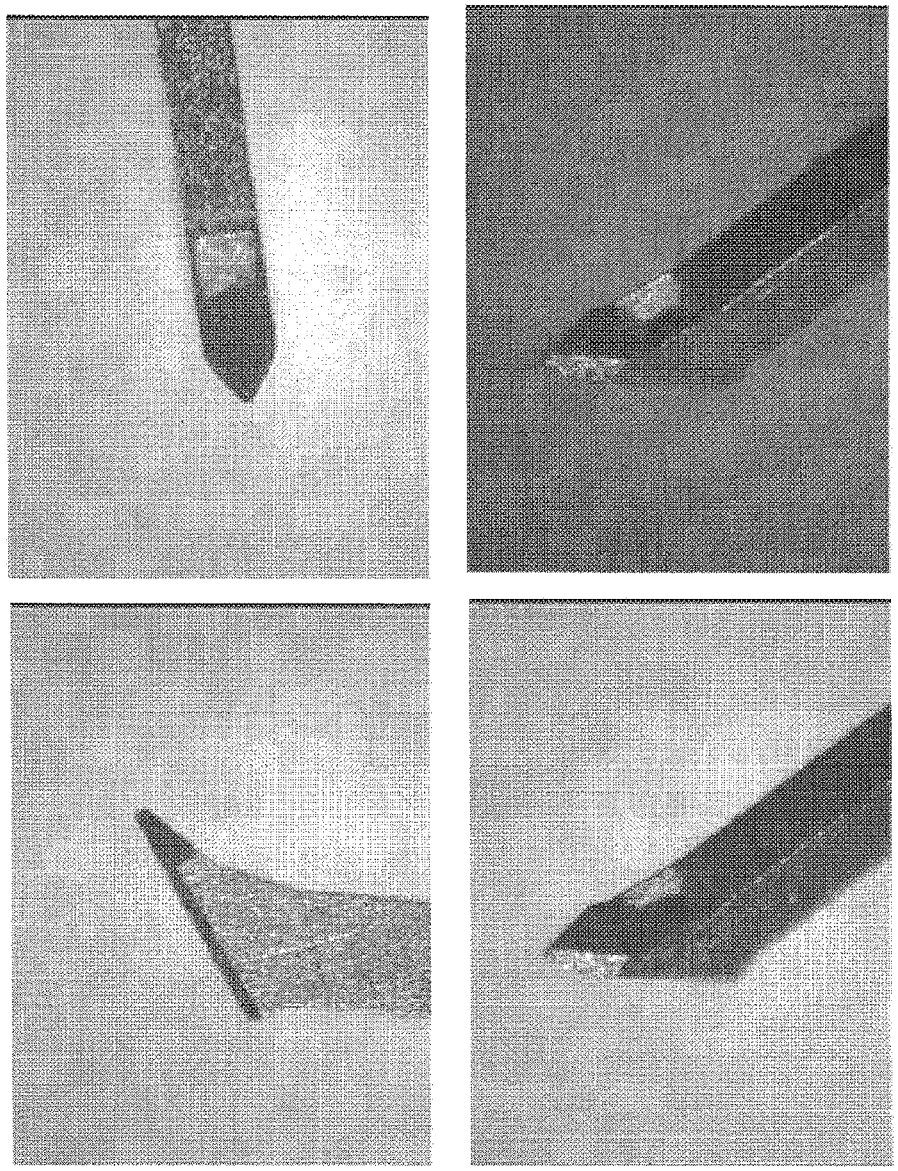
FIG. 5 shows four different angles of a fabricated embodiment of the present invention under 40× magnfication.
Figure 6:
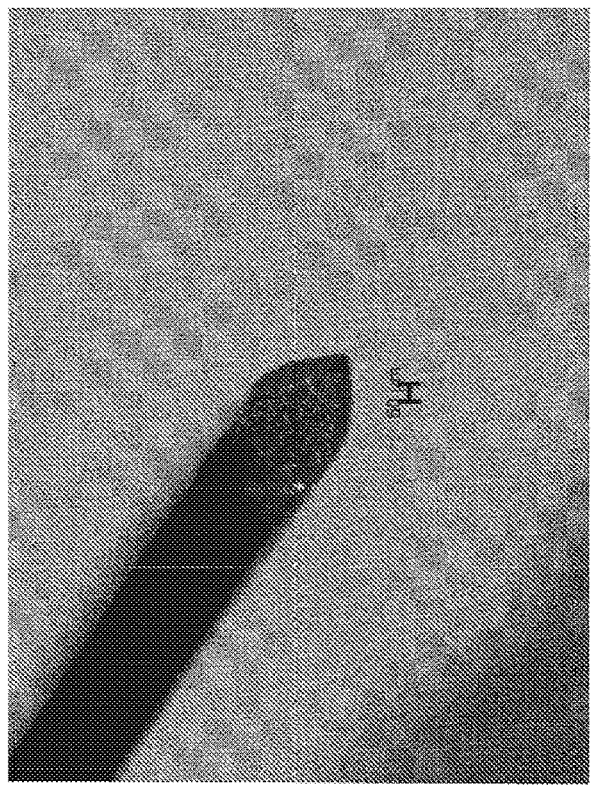
FIG. 6 shows two different angles of a fabricated embodiment of the present invention under 40× magnfication. A size scale indicates proportsions.
Figure 6:
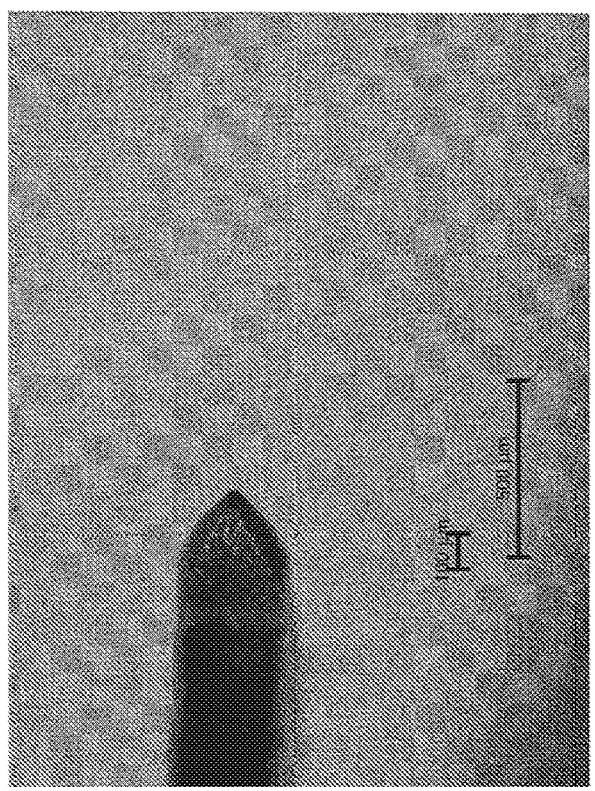
Figure 7:
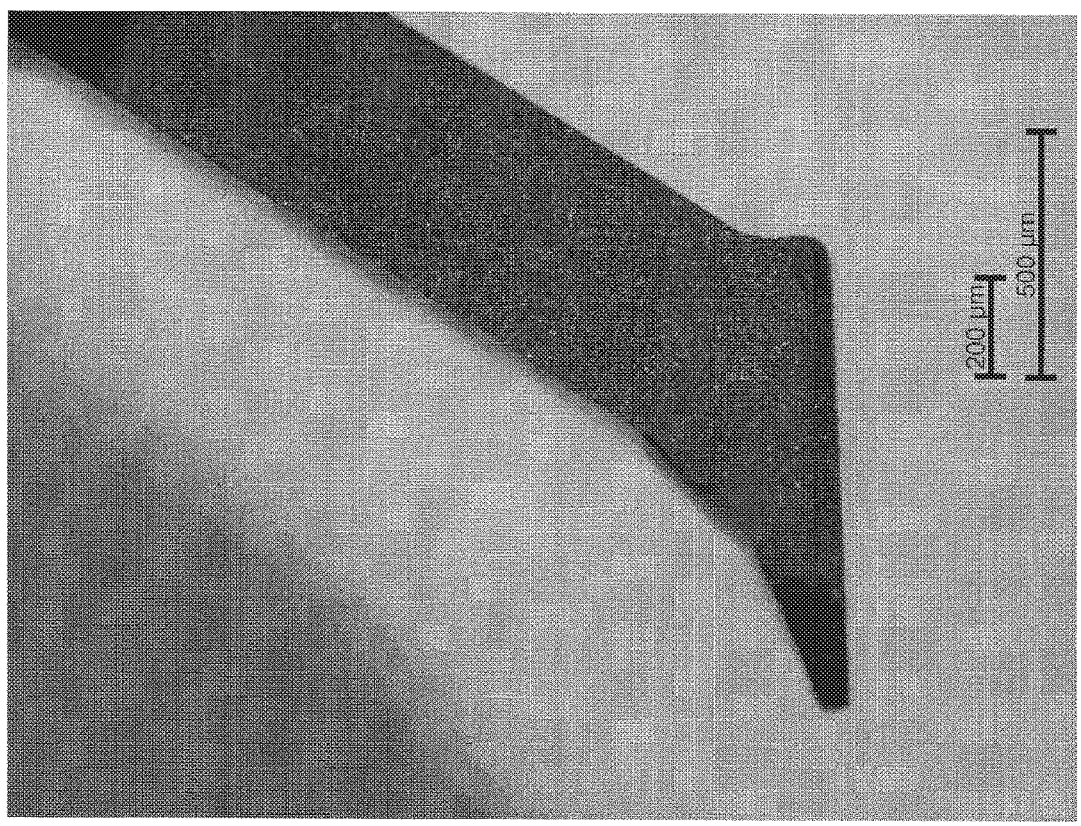
FIG. 7 shows a side angle of a fabricated embodiment of the present invention under 40× magnfication. A size scale indicates proportions.
Figure 8:
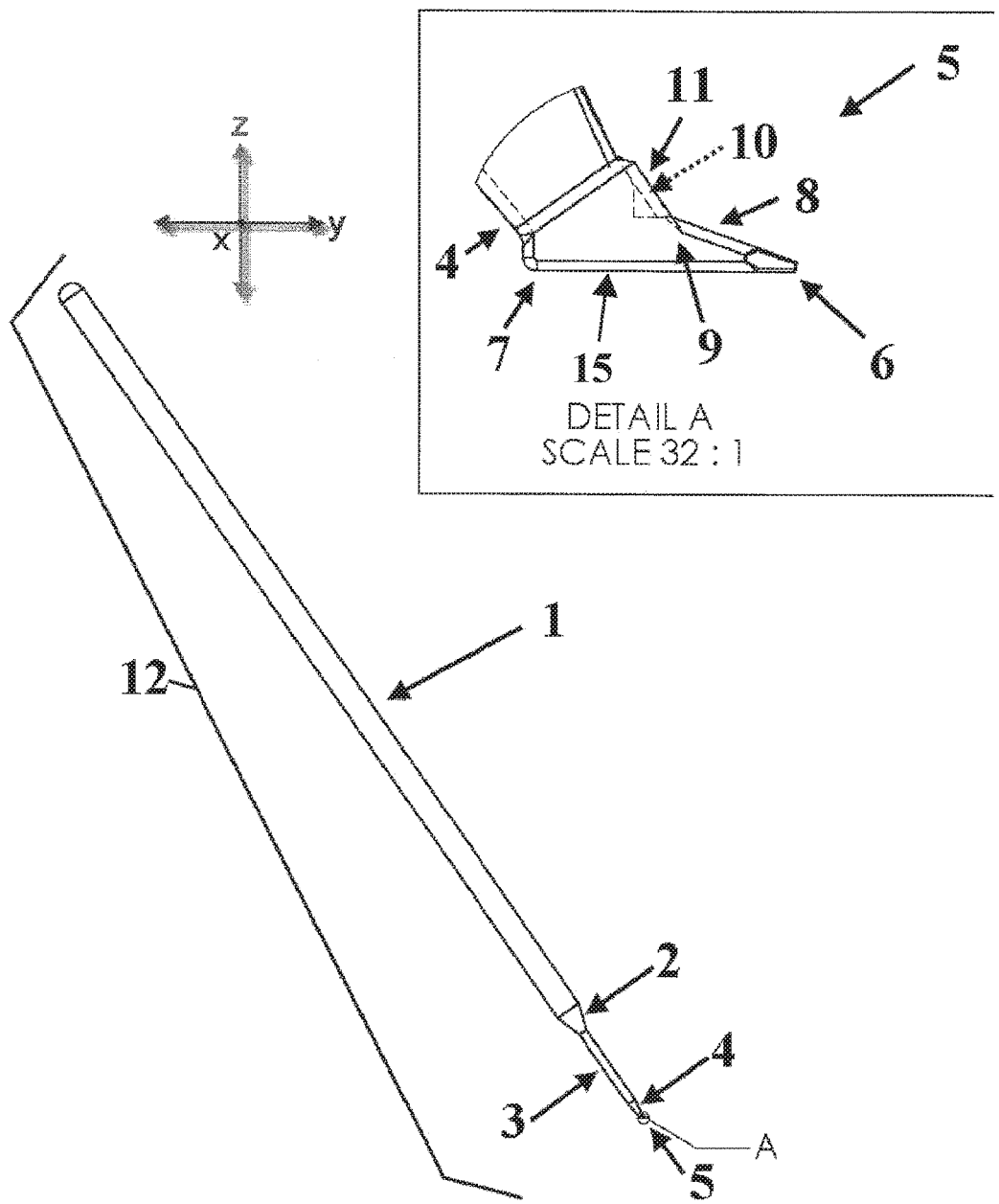
FIG. 8 shows an angled, side view of one embodiment of the device with an enlarged detailed view of the operative end of the device with the beveled platform.
Figure 9:
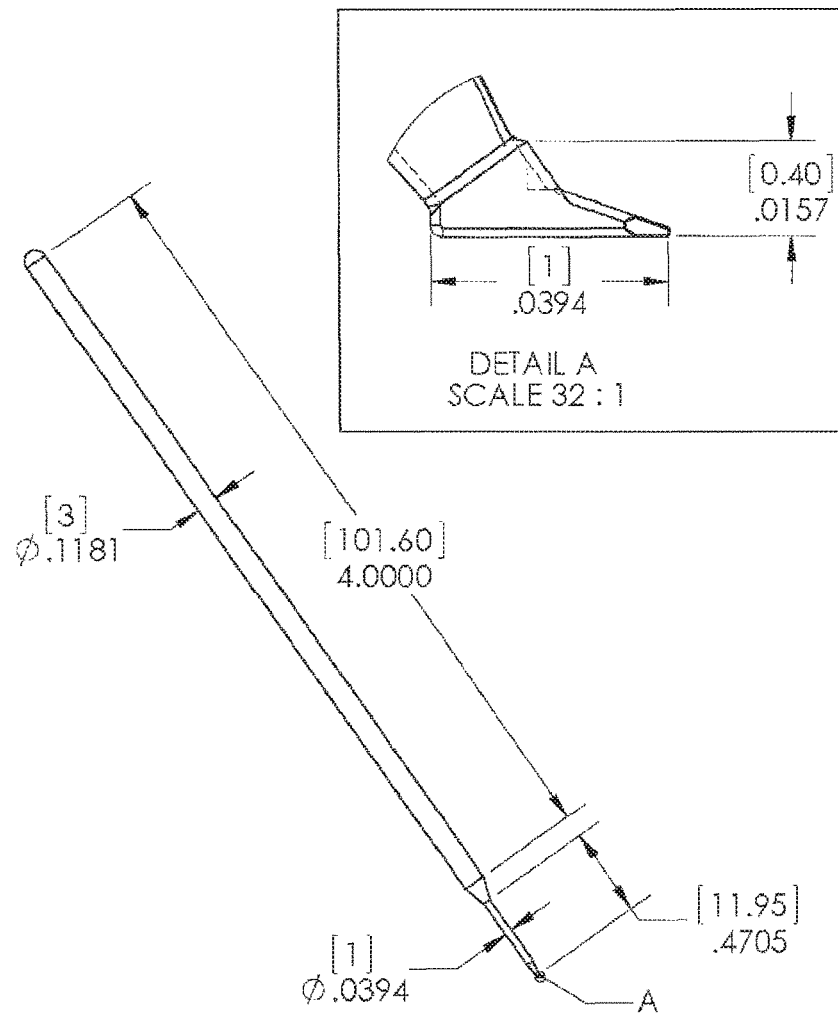
FIG. 9 shows an angled, side view of one embodiment of the device with an enlarged detailed view of the operative end of the device with the beveled platform. Measurements of specific parts are indicated.

In an effort to provide a low-cost MIGS device that can be widely used by ophthalmic surgeons, one embodiment of the present invention contemplates a novel medical-grade stainless steel dual-blade device that can successfully remove TM with no discernible collateral damage was designed. In one embodiment, the device comprises a unique dual-edge blade design using precise geometries to allow for more complete removal of TM tissue (FIG. 4). Although it is not necessary to understand the mechanism of an invention, it is believed that the procedure is performed from an ab interno approach and is viscoelastic to maintain the anterior chamber. For example, the size and tip of the blade can allow for a smooth entry into the Schlemm's canal, similar to techniques used for traditional goniotomy procedures. Once in place, the tip is advanced through the Schlemm's canal and the TM is elevated along a designed ramp that guides tissue toward a set of blades positioned specifically to incise and remove TM. In contrast to the Trabectome® footplate, which is juxtaposed between the outer wall of the Schlemm's canal and the inner wall of the Schlemm's canal to provide protection during cautery, the dual-blade device transects TM and elevates TM off of the outer wall of the Schlemm's canal. Although it is not necessary to understand the mechanism of an invention, it is believed that by elevating the TM along the ramp of the device as it moves forward leads to maximal tissue removal when incised by the superiorly placed and strategically angled dual blades. It is further believed that the angle between the distal cutting edge and the handle is engineered to allow maximal angle treatment through 1 incision while avoiding trauma to the cornea above or the scleral spur below. The excised TM may then be removed from the eye with forceps or aspirated during the irrigation/aspiration phase if combined with cataract extraction. In addition, the device of the present invention can easily pass through clear corneal incisions as small as 1.2 mm, thus obviating the need for additional incisions when coupled with phacoemulsification.

Another device known in the art that has been used for ab interno trabeculectomy is known as the "gonioscraper," as described by Jacobi and associates [20]. This device consisted of a handle and curette tip and was used to remove TM by scraping the curette within the Schlemm's canal. The curette tip is in line with the handle and does not conform to the geometry of the drainage angle and adjacent structures. After promising preclinical experiments, a nonrandomized clinical trial of 25 eyes was completed [21]. Preoperative IOP was 34.7±7.1 mm Hg on 2.2±0.56 medications and mean follow-up time was 32 months. Based on the success criteria of postoperative IOP of 19 mm Hg or less with 1 pressure-reducing agent, 15 eyes (60%) were successful. Nonetheless, complications developed in some patients including localized Descemet membrane detachments and/or anterior chamber bleeding. Histologic analysis of banked human eyes treated with the curettage showed successful removal of TM tissue, but with damage to the septa and endothelium of the external and posterior wall of the Schlemm's canal [20]. In the data presented herein, similar damage to adjacent sclera was also observed when using the MVR blade, but was notably absent with use of one embodiment of a dual-blade device as contemplated by the present invention. In addition, the present invention contemplates a novel blade device geometry designed to minimize any impact to adjacent tissues such as Descemet membrane by leveraging specific angles between the handle and the distal blade as well as use of specific angles between the cutting blade and the adjacent cutting tip.

There have been reports of both success and failure with the Trabectome® device over the past few years [14-17, 22]. In a recent retrospective study of Trabectome® versus ab externo trabeculectomy, Jea and associates found poor success rates in eyes treated with Trabectome® at 2 years [14]. Of the 115 eyes treated with Trabectome®, only 22.4% achieved success with failure defined as IOP >21 mm Hg or <20% reduction in IOP. It is conceivable that, after initial opening of the canal with TM removal, the residual leaflets occlude the Schlemm's canal and/or the more distal collector channels, leading to failure of the intervention. This mechanism of failure after Trabectome® treatment would be overcome by the dual-blade device, as a more complete removal of TM tissue is produced without residual leaflets.

There are several practical advantages of a dual blade device, as contemplated herein, for use in ab interno trabeculectomy. First, a dual blade device may be reusable and can be added to a standard cataract surgical tray. Second, the lack of moving parts or the need for coupled irrigation or a separate power source allows for inexpensive manufacturing and rapid acquisition of surgical expertise. This would permit easy, economical access to a new technique, especially in underserved locations around the world. For comparison, the conventional Trabectome® device requires a substantial initial investment for the irrigation/aspiration unit and generator in addition to the cost of one-time-use items such as the hand piece and tubing. The simple design and material requirements of dual-blade device embodiments would be more economical. Finally, in contrast to other techniques for TM removal, embodiments of dualblade device designs conform to the Schlemm's canal anatomy, minimizes damage to adjacent tissues, and provides excellent control over excised tissue. In conclusion, the presented novel dual-blade MIGS device represents a novel technique to perform ab interno trabeculectomy with or without concomitant cataract extraction. In some embodiments, the dual-blade devices are capable of a more complete removal of TM tissue from the anterior chamber angle in a simple and inexpensive manner as compared to conventional devices. Perfusion eye studies support the potential for significant IOP reduction with this technique (supra).

DESCRIPTION OF THE PREFERRED EMBODIMENT

1. Background

A goniotomy is generally referred to as a surgical procedure primarily used to treat congenital glaucoma. It can be caused by a developmental arrest of some of the structures within the anterior (front) segment of the eye. These structures include the iris and the ciliary body, which produces the aqueous fluid needed to maintain the integrity of the eye. These structures do not develop normally in the eyes of patients with isolated congenital glaucoma. Instead, they overlap and block the trabecular meshwork, which is the primary drainage system for the aqueous fluid. Because of this blockage, the trabecular meshwork itself becomes thicker and the drainage holes within the meshwork are narrowed. These changes lead to an excess of fluid in the eye, which can cause pressure that can damage the internal structures of the eye and cause glaucoma.

In general, congenital glaucoma is caused by a decrease in or even a complete obstruction of the outflow of intraocular fluid. The ocular syndromes and anomalies that predispose a child to congenital glaucoma include the following: Reiger's anomaly; Peter's anomaly; Axenfeld's syndrome; and Axenfeld-Rieger's syndrome. Systemic disorders that affect the eyes in ways that may lead to glaucoma include Marfan's syndrome; rubella (German measles); and the phacomatoses, which include neurofibromatosis and Sturge-Weber syndrome. Since these disorders affect the entire body as well as the eyes, the child's pediatrician or family doctor will help to diagnose and treat these diseases.

One purpose of a goniotomy is to clear the obstruction to aqueous outflow from the eye, which in turn lowers the intraocular pressure (TOP). Although it is not necessary to understand the mechnaims of an invention, it is believed that lowering the IOP helps to stabilize the enlargement of the cornea and the distension and stretching of the eye that often occur in congenital glaucoma. The size of the eye, however, may not return to normal. Most importantly, once the aqueous outflow improves, damage to the optic nerve is halted or reversed. The patient's visual acuity may improve after surgery.

Before the surgeon begins the procedure, the patient may be given miotics, which are drugs that cause the pupil to contract. The partial closure may improve the surgeon's view of and access to the trabecular meshwork; it may also protects the lens of the eye from trauma during surgery. Other drugs may be administered to lower the intraocular pressure. Goniotomy procedures may be done without use of miotics. In one embodiment, the current invention may be used in the setting of a dilated (non-miotic) pupil, as can devices described as prior art.

Once the necessary drugs have been given and the patient is anesthetized, the surgeon may use forceps or sutures to stabilize the eye in the correct position. The patient's head may be rotated away from the surgeon so that the interior structures of the eye are more easily seen. Next, with either a knife-needle or a goniotomy knife, the surgeon punctures the cornea while looking at the interior of the eye through a microscope or a loupe. An assistant may use a syringe to introduce fluid into the eye's anterior chamber through a viscoelastic tube as the surgeon performs the goniotomy.

A gonioscopy lens may be then placed on the eye. As the eye is rotated by an assistant, the surgeon sweeps the knife blade or needle through 90-120 degrees of arc in the eye, making incisions in the anterior trabecular meshwork, avoiding the posterior part of the trabecular meshwork in order to decrease the risk of damage to the iris and lens. Endoscopic visualization may also be used to guide cutting. In one embodiment, the device of the current invention may be place at the end of an endoscope, precluding the need for a gonio lens during treatment.

Once the knife and tubing are removed, saline solution may be introduced through the hole to maintain the integrity of the eye and the hole is closed with sutures. The surgeon then applies antibiotics and corticosteroids to the eye to prevent infection and reduce inflammation. The head may be then rotated away from the incision site so that blood cannot accumulate. The second eye may be operated on at the same time. If the procedure needs to be repeated, another area of the eye may be treated.

Previous devices have been described in Sorensen et al., "Tubular Cutter Device and Methods For Cutting and Removing Strips of Tissue from the Body of a Patient," U.S. Pat. No. 7,959,641 (Issued Jun. 14, 2011; [23]) Also see International Publication No. WO 2004/110501 [24] and United States Publication No. US 2007/0276420 related parts [25]). This reference discloses a device for cutting a strip of tissue with a width of about 50-200 µm from the trabecular meshwork. The device has a first and second cutting edge formed on the distal end of the cutting tube. The tip can be blunt and in some applications is configured and used to facilitate the insertion of the device into its intended location i.e. Schlemm's canal. Further, one or more bends or curves may be optionally formed to facilitate its use. The tip of the device may be advanced through the trabecular meshwork and into the Schlemm's canal thereby causing the cutting edges to cut a strip of the trabecular meshwork, thereby creating an opening for drainage of aqueous humor. While this reference teaches a cutting blade with dual cutting sides and a tip for placement into Schlemm's canal for removal of trabecular meshwork with optional bends/curvatures it does not specifically mention use of a 0.3 mm blade width.

Another device is described in Huculak, "Small Gauge Mechanical Tissue Cutter/Aspirator Probe for Glaucoma Surgery," United States Patent Publication No. US 2009/0287233 [26]. This reference discloses use of a small gauge mechanical tissue cutter/aspirator probe to remove trabecular meshwork. The probe can be guided into Schlemm's canal and moved in a forward motion following the curvature of the trabecular meshwork. The motion causes the trabecular meshwork to be fed into the cutting port of the cutter, thereby cutting and removing the trabecular meshwork that blocks the outflow of aqueous humor. Due to the size of Schlemm's canal, it is preferable to have the distal end of the outer cannula measure about 0.25 to 0.36 mm diameter. The cannula can be tapered so its distal end measures about 0.25 to 0.36 mm (Schlemm's canal is about 0.3 mm). Further, the leading edge can be curved to enhance its ability to pierce the trabecular meshwork. While the reference teaches use of a small gauge cutter with a diameter of about 0.25 to 0.36 mm with a sharp or blunt leading edge for piercing the trabecular meshwork and entry into Schlemm's canal with a cutting port to cut the trabecular meshwork it does not per se teach a dual sharp edge cutting blade.

Another device is described in Baerveldt et al., "Minimally Invasive Glaucoma Surgical Instrument and Method," United States Patent Publication No. US 2011/0077626 [3] (Also see U.S. Pat. No. 7,785,321 [6] and U.S. Pat. No. 6,979,328 [2]; and United States Patent Publication No. US 2006/0106370 [4] and US 2002/0111608 [5] selected parts). This reference discloses use of a cutting probe to cut and remove trabecular meshwork. The probe comprises a tip that is approximately 25 gauge (about 0.5 mm). The tip further comprises a footplate that serves as a guide into Schlemm's canal. The sharpened end of the footplate is used to pierce the trabecular meshwork. The trabecular meshwork is cut using a rotatable blade or cut in a guillotine fashion. While the reference discloses use of a cutting probe with a tip approximately 25 gauge including a footplate for piercing the trabecular meshwork and targeting Schlemm's canal it does not per se mention use of a dual sharp edge cutting blade sized for navigating Schlemm's canal (0.3 mm).

Another device is described in Huculak, "Small Gauge Mechanical Tissue Cutter/Aspirator Probe for Glaucoma Surgery," International Publication No. WO 2009/140185 [27] (Also see European Patent No. EP 2303203 [28] selected parts). This reference discloses use of a small gauge mechanical tissue cutter/aspirator probe to remove trabecular meshwork. The probe consists of an outer cannula and an inner cannula. The inner cannula's distal end is configured to cut tissue when it enters port 310. The inner cannula is moved up and down to cut tissue. The outer cannula includes a retractable pick that has a sharp end for piercing the trabecular meshwork. Due to the size of Schlemm's canal, it is preferable to have the distal end of the outer cannula measure about 0.25 to 0.36 mm in diameter. The cannula can be tapered so its distal end measures about 0.25 to 0.36 mm (Schlemm's canal is about 0.3 mm). While the reference discloses use of a probe sized between 0.25 and 0.36 mm for piercing the trabecular meshwork and placement into the Schlemm's canal, it does not mention use of a dual sharp edge cutting blade with a curvature for navigating Schlemm's canal.

Another device is described in Bergheim, O. B. and Gharib, M. "Apparatus and Method for Treating Glaucoma," WIPO Patent WO/2001/078631 Application PCT/US2001/007398, filed Mar. 8, 2001. (Published Oct. 25, 2001) [29]. This reference discloses use of a cutting member positioned at the distal end of a tube consisting of a knife, a pointed guide member, and a sharpened distal end of said tube. The cutting member is configured to form an opening in the trabecular meshwork for placement of a seton into Schlemm's canal. The knife includes a microknife sized within the range of 20 to 40 gauge preferably 30 (0.3 mm) gauge. While the reference discloses use of a cutting member sized from 20 to 40 gauge for cutting the trabecular meshwork and delivery of a seton to Schlemm's canal it does not mention use of a dual sharp edge cutting blade with a curvature for navigating Schlemm's canal.

Another device is described in Skjaerpe, Finn, "Microsurgical Instrument," U.S. Pat. No. 4,501,274 [30] (Issued Feb. 26, 1985; also see European Patent No. EP 0073803 [31] selected parts). This reference discloses a microsurgical probe with a cutting member comprised of two knife blades protruding in different directions from the probe each with at least one sharp cutting edge. The cutting member has a double-cutting knife, where the two cutting edges are angularly separated such that they create a V-form adapted to the local anatomical features of the eye at the Schlemm's canal and the trabecular meshwork. The probe diameter is approximately 0.25 mm and the width of the knives is 0.3 to 0.5 mm. The knife blades also include a cutting edge on both sides so the probe can be pulled in both directions through the Canal of Schlemm. While the reference discloses a dual-knife with at least one sharp cutting edge for cutting the trabecular meshwork and the inner wall of Schlemm's canal it does not per se mention a curvature for navigating Schlemm's canal.

Another device is described in Conston et al., "Ophthalmic Microsurgical System," United States Patent Publication No. US 2006/0149194 [32] (Also see International Publication No. WO 2003/045290 [33], European Patent No. EP 1455698 [34] and Korean Patent No. KR 1020040058309 [35] selected parts). This reference discloses a microsurgical system with an outer microcannula sheath that includes an inner member that is sized to adapt to the Schlemm's canal that is about 50 to 200 microns in diameter. The inner member is in the range of 50-240 microns in outer diameter in order to fit within the outer cannula, which is 50-250 microns in inner diameter. The outer microcannula and inner member each are adaptable to the curvature of Schlemm's canal and the inner member optionally includes a cutting tool at the distal end with a diamond or sapphire tip or blade or similar element. While the reference discloses a micro sized probe for cutting trabecular meshwork and targeting Schlemm's canal it does not per se mention use of a dual sharp edge cutting blade for piercing the trabecular meshwork and targeting Schlemm's canal.

Another device is described in Conston et al., "Ophthalmic Microsurgical Instruments," United States Patent Publication No. US 2007/0073275 [36] (Also see International Publication No. WO 2004/093761 [37] and European Patent No. EP 1615604 [38] selected parts). This reference discloses a microsurgical instrument that can be directly inserted into Schlemm's canal to allow controlled treatment or removal of adjacent tissues such as TM. The instruments comprise an outer sheath microcannula and an inner member where the distal end of the instruments can be curved to approximate the curvature of Schlemm's canal. The instruments include a cutting means to excise targeted tissue. The microcannula is sized to accommodate the Schlemm's canal (approximately 200 microns in diameter) approximately ranging from 100 to 350 microns outer diameter. The distal tip of an inner member can be beveled or sharpened to provide a cutting action. While the reference discloses a micro sized probe for cutting trabecular meshwork and targeting Schlemm's canal it does not per se mention use of a dual sharp edge cutting blade for piercing the trabecular meshwork and targeting Schlemm's canal.

Another device is described in Huculak, "Pulsed Electric Field Probe for Glaucoma Surgery," United States Patent Publication No. US 2011/0230877 [39]. This reference discloses use of a small gauge pulsed electric field probe for removal of trabecular meshwork. The distal end of the probe includes a pick adapted to fit into Schlemm's canal so the electric pulsed field can be used to dissociate and remove the trabecular meshwork. The pick has a sharp end so it can pierce the trabecular meshwork and so the pick can be placed into the Schlemm's canal. The pick is retractable. The probe has a diameter between 0.25 and 0.36 mm. While the reference discloses use of a probe sized between 0.25 and 0.36 mm for piercing the trabecular meshwork and placement into the Schlemm's canal, it does not mention use of a dual sharp edge cutting blade with a curvature for navigating Schlemm's canal.

Another device is described in Pantcheva, M. B. and Kahook, M. Y. (2010) Ab Interno Trabeculectomy, *Middle East Afr. J. Ophthalmol.* 17(4), 287-289 [16]. This reference is a review of the Trabectome® device that may give some ideas on what devices in this category.

2. Traditional Incisional Goniotomy

Figure 20:
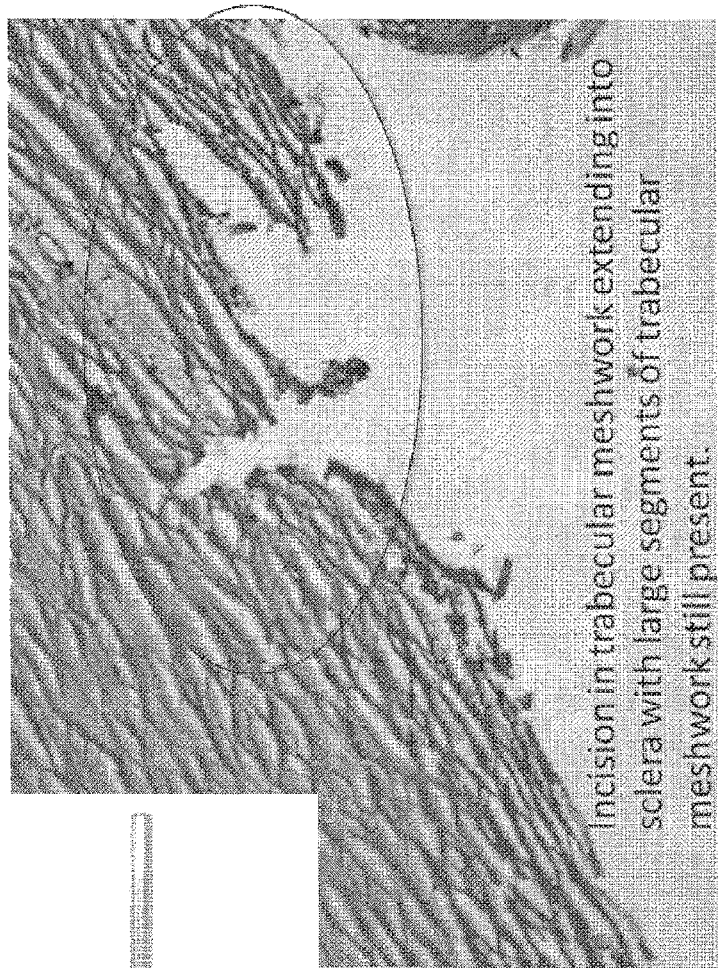
FIG. 20 shows an incision in trabecular meshwork extending into sclera with large segments of trabecular meshwork still present.

FIG. 20 shows an incision in trabecular meshwork extending into sclera with large segments of trabecular meshwork still present. For this procedure (considered the gold standard surgery for "cutting" through the trabecular meshwork and traditionally called "goniotomy") an MVR blade was used to incise the trabecular meshwork to create an opening into Schlemm's canal. In this photo, there is a histological sample from a procedure in which an incision exists through Trabecular meshwork and extends into sclera. There are large leaflets of trabecular meshwork remaining on either side of the incision. These leaflets scar down and close the opening that was created into Schlemm's canal. This preludes any long-term benefit in intraocular pressure lowering which is the goal of the surgery.

3. Procedure Using Trabectome®

For this procedure (designed to replace goniotomy and to improve upon that procedure by removing sections of trabecular meshwork) a Trabectome® device was used to engage the trabecular meshwork and cautery was applied to the trabecular meshwork. The circle shows an area where a small segment of trabecular meshwork was removed; however, there are large leaflets of trabecular meshwork remaining and charred tissue on either side of the treatment area.

Figure 21:
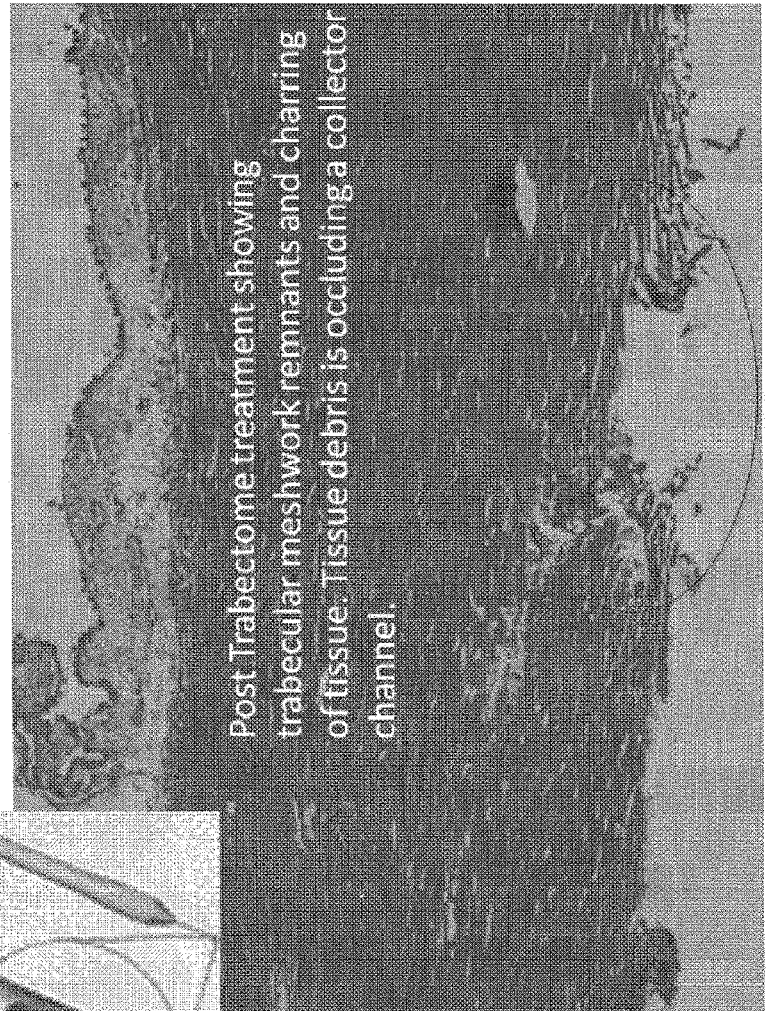
FIG. 21 shows post-Trabectome® treatment showing trabecular meshwork remnants and charring of tissue. Tissue debris is occluding a collector channel.
Figure 21:
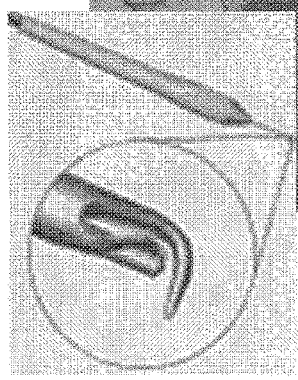

FIG. 21 shows post Trabectome® treatment showing trabecular meshwork remnants and charring of tissue. Tissue debris is occluding a collector channel this device "burns" tissue and the burning of tissue creates inflammation that leads to more scar formation that leads to failure of the surgically induced opening into Schlemm's canal. In addition, due to cautery, many bubbles are formed during the procedure that makes visualization difficult during the actual procedure. These issues do not occur with the current invention device, which is a major advantage. A representative photo of the Trabectome® is in FIG. 21

4. The Dual Blade Device of the Present Invention

Figure 22:
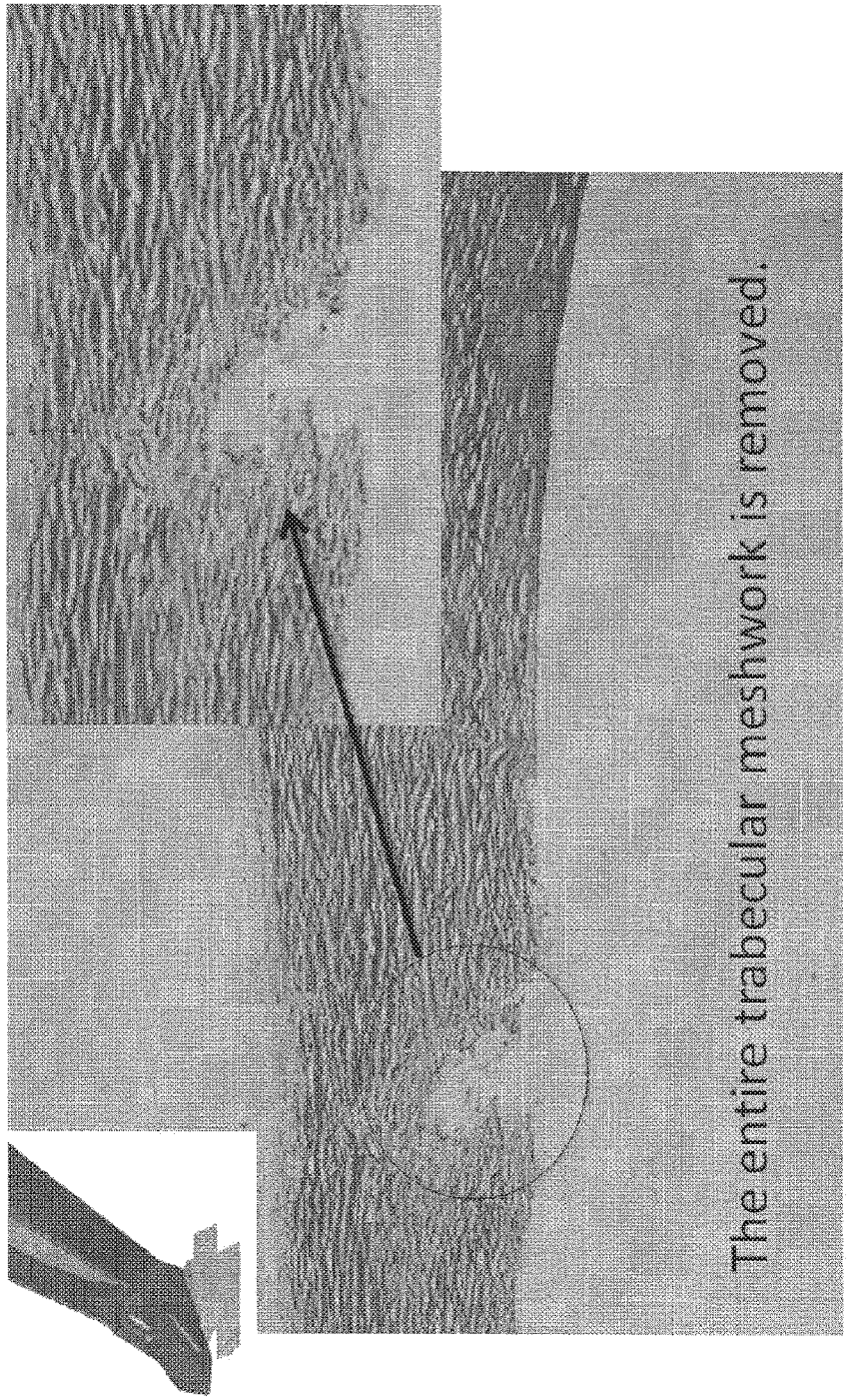
FIG. 22 shows tissue after treatment with the current invention device.

FIG. 22 shows tissue after treatment with one embodiment of a currently contemplated device. The data shows complete removal of trabecular meshwork with no remaining leafletswithout any evidence of tissue burning. The inset photo in FIG. 22 shows a close up of the circled area. A representative photo of the present invention device is in the inset on the left of FIG. 22.

Figure 23:
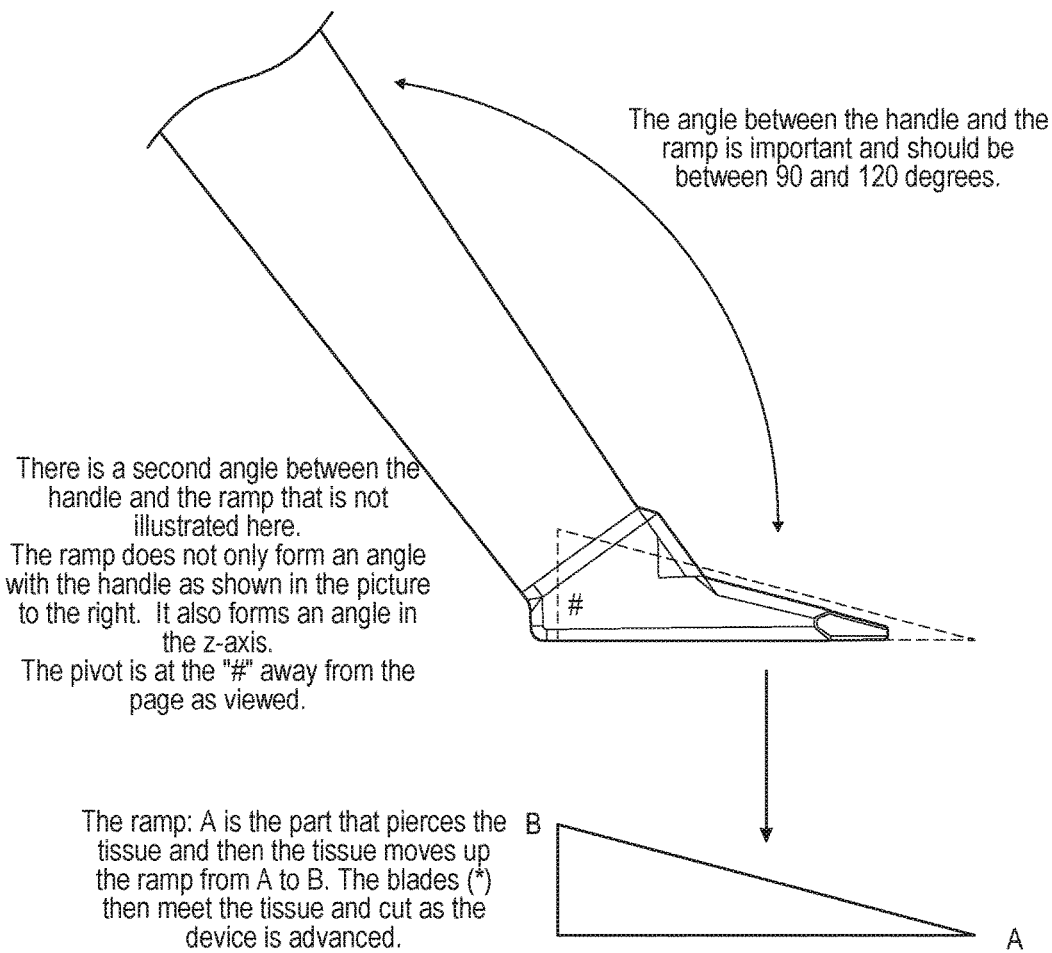
FIG. 23 shows another description of the configuration of the dual blade device of the current invention.

There is a second angle between the handle 1 and the ramp that is not illustrated in FIG. 23. The ramp does not only form an angle with the handle 1 as shown in the picture to the right in FIG. 23. It also forms an angle in the z axis. (The pivot is at the "#") away from the page as viewed. In one embodiment, the angle between the handle 1 and the ramp ranges between approximately 90 and 120 degrees. Although it is not necessary to understand the mechanism of the invention, it is belived that, ramp: A pierces the tissue wherein the tissue then slides up the ramp from A to B. The blades (*) then cut the tissue as the device is advanced.

The disadvantage of a conventional blade as described by Baerveldt [2-6] where the foot plate is sitting in Schlemm's canal. Because there is no ramp and no second angle between the tip and the handle, a second angle would have a pivot at the "*" which would create a pivot of the device inferiorly at the ramp. Baerveldt [2-6] demonstrates how the foot-plate is sitting in Schlemm's canal, but there is no ramp and there is no second angle between the tip and the handle. In the current invention, a second angle would have a pivot at the "*" which would create a pivot of the device inferiorly at the ramp.

Figure 24:
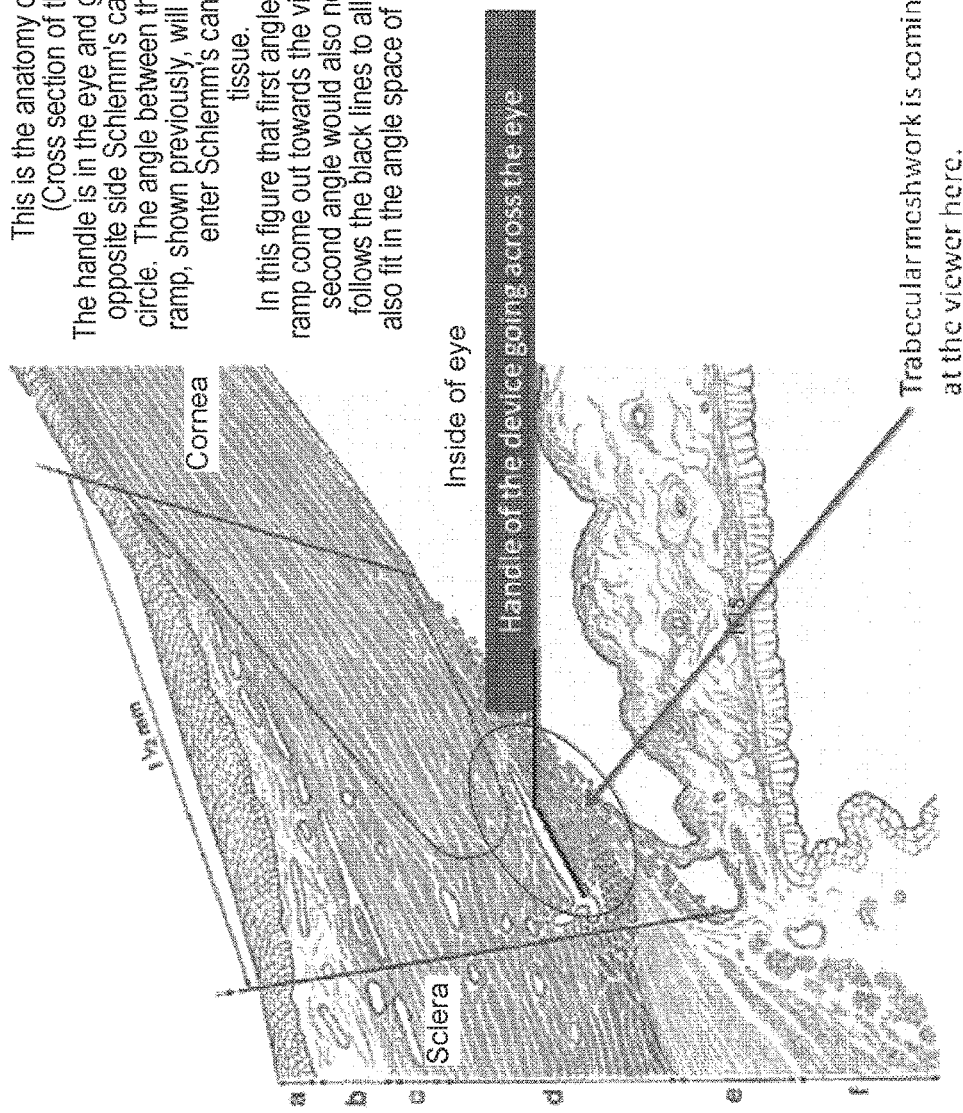
FIG. 24 shows the anatomy of interest. (Cross section of the eye) the handle 1 is in the eye and going across to the opposite side Schlemm's canal outlined by a circle. The angle between the handle 1 and the ramp will allow the blade to enter Schlemm's canal and cut tissue. That first angle would make the ramp come out towards the viewer. However, a second angle would also need to exist that follows the black lines to allow the device to also fit in the angles space of Schlemm's canal.

FIG. 24 shows a cross section of the eye where one embodiment of handle 1 is in the eye and going across to the opposite side Schlemm's canal outlined by a circle. The angle between the handle 1 and the ramp will allow the blade to enter Schlemm's canal and cut tissue. In this figure, that first angle would make the ramp come out towards the viewer. However, a second angle would also need to exist that follows the black lines to allow the device to also fit in the angles space of Schlemm's canal.

5. Use of the Device

The device may be introduced through a clear corneal incision (incision size between 0.5 and 2.8 mm in width) and advanced through the anterior chamber either across the pupil or across the body of the iris to engage the trabecular meshwork (TM) on the opposite side of the anterior chamber. The anterior chamber may be filled with viscoelastic to stabilize the chamber during the procedure. Once the TM is reached, the tip of the device may be then used to enter into Schlemm's canal (SC) and the ramp may be used to elevate the TM and present tissue to the dual blades as the device advances clockwise or counterclockwise. The angle of the distal cutting portion is angled so that the dual blades are placed in optimum cutting position. This angle may be such that the cutting tip bends to conform to the area between schwalbe's line and the scleral spur (SS), an area that encompasses SC. SC is narrow near the cornea and wider near the SS and thus an angled tip is best to present the tissue to the two edges of the TM. The ramp of the cutting tip may be angled so that the tissue is constantly elevated towards the blade as the tip is advanced in circumferential pattern. Endoscopic visualization may also be used to guide cutting. In one embodiment, the device of the current invention may be place at the end of an endoscope, precluding the need for a gonio lens during treatment. In one embodiment, the device of the current invention may be place at the end of an endoscope and the TM may be engaged under direct visualization of the endoscope camera.

The tip may be formed of various metals or polymers that are rigid enough to support elevation of tissue such as TM. The blades may be made of the same materials as the distal tip and handle 1 or might be of a separate material that allows for greater tolerances for a razor edge (stainless steel or titanium). Shape memory polymers or alloys could be utilized to enhance functionality of the device by allowing for a change in confirmation after placing the device in the eye and exposing it to body heat. A movable sheath might be employed to cover the distal cutting tip during the insertion and removal steps from the eye so that the tip is not injured by movement across the clear corneal wound.

The device can be made of different colors such as Blue or Black so that it can be visualized through the semi translucent TM tissue for better guidance.

The device could have a distal port that allows for injection of fluid to delivery local medication or other therapeutic agents or to wash away reflux of blood that occurs during this type of procedure. The ultimate goal of this procedure may be to remove entire segments of TM without leaving leaflets of tissue behind (something that occurs with other devices that cut TM without conforming to the space of interest). The procedure might be combined with cataract extraction and can be performed before or after the cataract extraction and while the pupil is dilated. The procedure might be coupled with other intraocular surgery such as iris or vitreous/retina based procedures.

Conditions that might benefit from use of this device include:
1. Primary open angle glaucoma
2. Normal or Low tension glaucoma
3. Pseudoexfoliation glaucoma
4. Pigment dispersion glaucoma
5. Angle closure glaucoma (acute, subacute, chronic)
6. Neovascular or inflammatory glaucoma
7. Ocular hypertension
8. Other types of glaucoma that are related to high intraocular pressure The device could be used for research purposes to harvest TM or other small sheath of tissue for lab based studies or to harvest cells for in vitro culture needs. The device can be used to cut Anterior Synechiae or other cellular or fibrovascular membranes over the drainage angle such as those seen with ICE syndrome or neovascular glaucoma.

A goniotomy is simply an incision of the TM to cut it into two leaflets, it is the basic form of cutting TM that all other devices are trying to improve upon. Since it is just an incision, it leaves the entire tissue behind (albeit segmented) and then the tissue scars down and the eye pressure goes up anyway. This may be why "newer" devices are trying to cut and remove the actual TM from the area over Schlemm's canal. The complete removal of TM without leaving leaflets is one key feature differentiating the current invention's device from standard blade goniotomy as described in the patent to Baerveldt [2] (now marketed under the name "Trabectome®"). The anatomical design of the current invention's device may be better suited for effective removal of complete strips of tissue, in particular the TM, with minimal to no traumatic impact on the surrounding tissue.

6. Detailed Description of the Invention

The following detailed description, and the drawings to which it refers, are provided for the purpose of describing and illustrating certain preferred embodiments or examples of the invention only, and no attempt has been made to exhaustively describe all possible embodiments or examples of the invention. Thus, the following detailed description and the accompanying drawings shall not be construed to limit, in any way, the scope of the claims recited in this patent application and any patent(s) issuing there from.

This invention is in the field of surgical medicinal intervention. For example, the present invention relates to a microsurgical device and methods of its use for treatment of various medical conditions including but not limited to eye diseases, such as glaucoma, using minimally invasive surgical techniques. Specifically, the device may be a dual-blade device for cutting the trabecular meshwork (TM) in the eye. In particular, the device may have a device tip providing entry into the Schlemm's canal via its size (i.e., for example, between approximately 0.3-0.2 mm width) and a configuration where the entry blade tip curves up providing a ramp-like action for cutting the TM.

Specific advantages of some embodiments described herein as compared to other conventional devices include but are not limited to:
1. No mechanically moving parts
2. No cautery or burning of tissue
3. Two blades are in place on the sides of the device that cut the trabecular meshwork (TM) in a precise fashion leaving little TM behind (current devices leave a lot of TM behind that then scars over)
4. The entry into Schlemm's canal is done with use of the blade tip similar to what has been described for decades in standard goniotomy. The other devices use a non-blade footplate to enter Schlemm's canal.
5. The dimensions of the device allow for complete cutting and fit in Schlemm's canal with precision.
6. The tip of the blade ramps up to the two side blades forming a curve that presents the TM to the two slide blades, which then allows for more precise cutting.

Figure 17:
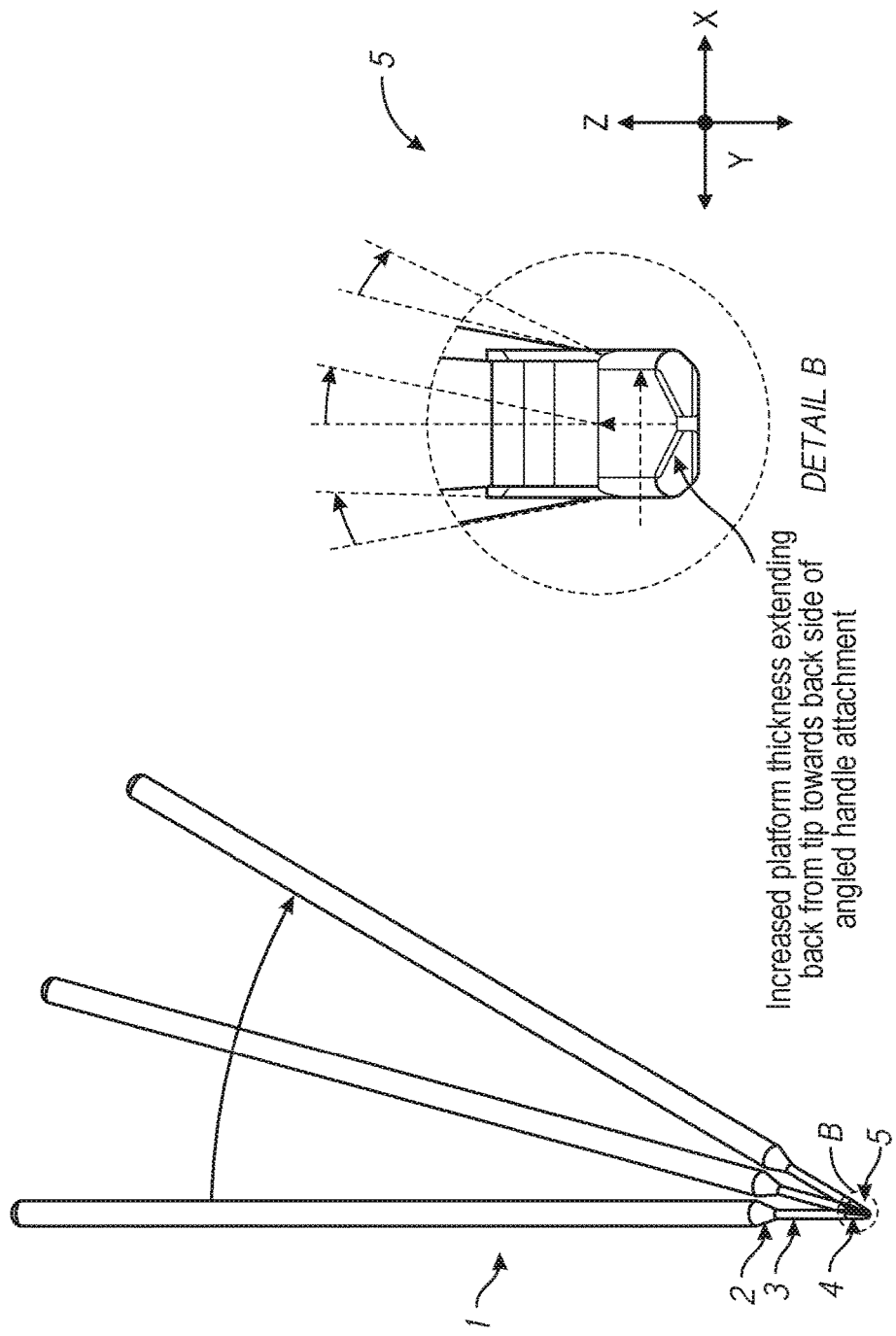
FIG. 17 shows a front face view of one embodiment of the device with an enlarged detailed view of the operative end of the device with the beveled platform 5. Shown are examples of the different angles of attachment of the handle 1 to the beveled platform 5 clockwise 0, 15, and 30 degrees relative to the Z-axis and X-axis. The increased platform thickness is also indicated as the platform extends from the insertion tip 6 towards the back of the platform 7 and from the first side (on the right) to the second side (on the left).
Figure 18:
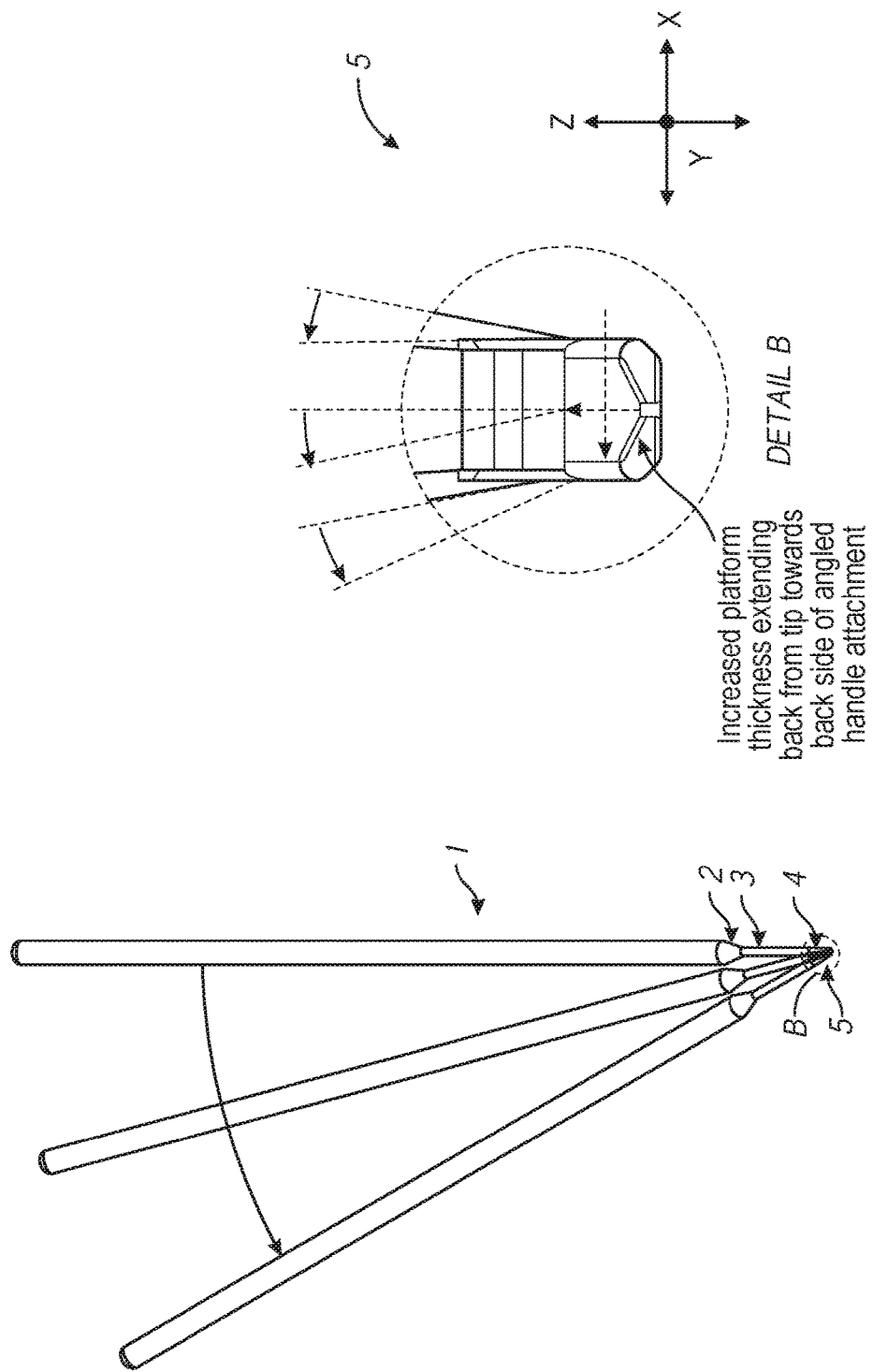
FIG. 18 shows a front face view of one embodiment of the device with an enlarged detailed view of the operative end of the device with the beveled platform 5. Shown are examples of the different angles of attachment of the handle 1 to the beveled platform 5 counterclockwise 0, 15, and 30 degrees relative to the Z-axis and X-axis. The increased platform thickness is also indicated as the platform extends from the insertion tip 6 towards the back of the platform 7 and from the second side (on the left) to the first side (on the right).
Figure 19:
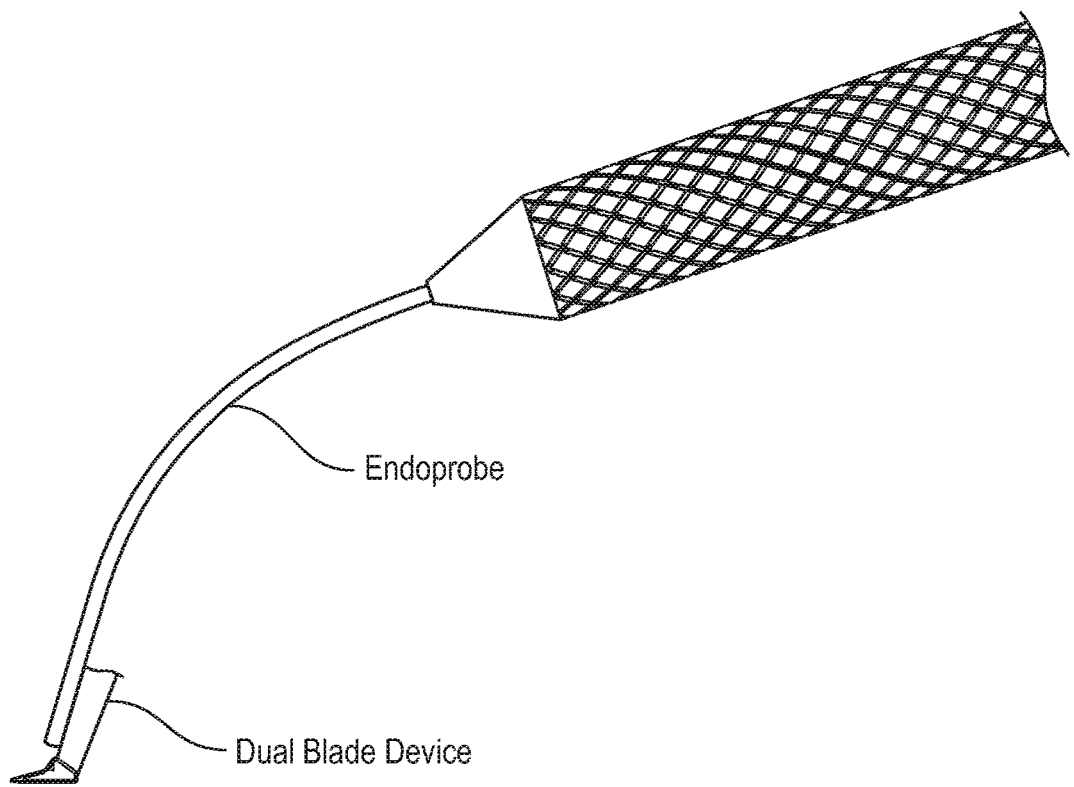
FIG. 19 shows one possible version of the device wherein it is integrated into an endoscope.

In one embodiment, the invention relates to a device 12 comprising: a handle 1 that necks down to a tool shaft 3 by a first interface 2 wherein said tool shaft widens into a beveled platform 5 by a second interface 4, wherein said beveled platform comprises a insertion blade tip 6 on a distal end of the beveled platform comprising a ramp from said insertion blade tip back towards the posterior end the beveled platform, and a first lateral blade 10 and second lateral blade 11 along the sides of said beveled platform. In one embodiment, said sides of said beveled platform comprise a first side 8 and a second side 9. In one embodiment, said first lateral blade 10 and second lateral blade 11 are in a perpendicular alignment to the bottom of the beveled platform. In one embodiment, the invention relates to a device 12 comprising a handle 1 and a beveled platform 5, wherein said platform 5 is set at a specific angle and orientation relative to said handle 1. In one embodiment, the invention relates to a device 12 comprising a handle 1 and a beveled platform 5, wherein said platform 5 freely rotates in at least two dimensions. In one embodiment, said handle 1 and beveled platform 5 are operably attached at an angle ranging between 90 and 120 degrees in the Y-Z axis (shown in FIG. 15). In one embodiment, said handle 1 and beveled platform 5 are operably attached at an angle ranging between 90 and 180 degrees in the X-Z axis (shown in FIG. 10). In one embodiment, said platform 5 freely rotates in an X-Y dimension relative to said handle 1. In one embodiment, said platform 5 remains at a fixed angle in the X-Y, X-Z, and Y-Z dimensions relative to said handle 1 (shown in FIG. 15). In one embodiment, said platform 5 freely rotates in a positive Z dimension relative to said handle 1. In one embodiment, said beveled platform 5 comprises a first end/beveled platform tip/insertion blade tip 6 and a second end/back of the beveled platform 7, wherein said second end/back of the beveled platform 7 is between 2 and 30 times greater in thickness relative to said first end/beveled platform tip/insertion blade tip 6. In one embodiment, the dimensions of the beveled platform 5 are dictated by the formula $A^2+B^2=C^2$, wherein A is the length of said beveled platform 5 from said insertion blade tip 6 to the back of the beveled platform 7, B is the height of the beveled platform 5 and C is the length of the ramp. In one embodiment, the height of said beveled platform 5 is not to exceed 0.5 millimeters. In one embodiment, the length of said beveled platform 5 from said insertion blade tip 6 to the back of the beveled platform 7, is not to exceed 1.0 millimeters. In one embodiment, said first end/beveled platform tip/insertion blade tip 6 comprises a fine surgical lancet. In one embodiment, said first end/beveled platform tip/insertion blade tip 6 comprises an angle of between 20 and 90 degrees. In one embodiment, said beveled platform 5 increases in thickness from a fine blade tip towards the second end/back of the beveled platform 7 in the direction of the Y-axis. In one embodiment, said first end/beveled platform tip/insertion blade tip 6 comprises a pointed tip with fine edges of surgical sharpness. In one embodiment, said first end/beveled platform tip/insertion blade tip 6 comprises a lancet. In one embodiment, said beveled platform 5 further comprises a first blade 10 and a second blade 11. In one embodiment, said first blade 10 is attached to a first side 8 of said second end/back of the beveled platform 7. In one embodiment, said first blade 10 and beveled platform 5 are operably attached at an angle ranging between 90 and 180 degrees in the Y-Z axis (shown in FIG. 15). In one embodiment, said angle is preferably between 90 and 120 degrees in the Y-Z axis (shown in FIG. 15). In one embodiment, said second blade 11 and beveled platform 5 are operably attached at an angle ranging between 90 and 120 degrees in the Y-Z axis (shown in FIG. 15). In one embodiment, said first blade 10 and handle 1 are operably positioned at an angle ranging between 90 and 120 degrees in the Y-Z axis (shown in FIG. 15). In one embodiment, said second blade 11 and handle 1 are operably positioned at an angle ranging between 90 and 120 degrees in the Y-Z axis (shown in FIG. 15). In one embodiment, said second blade 11 is attached to a second side 9 of said second end/back of the beveled platform 7. In one embodiment, said beveled platform 5 increases in thickness from said second side 9 towards the first side 8 in the direction of the X-axis (shown in FIG. 17). In one embodiment, said beveled platform 5 increases in thickness from said second side 9 towards the first side 8 in the direction of the X-axis and said beveled platform 5 increases in thickness from a fine blade tip of the first end 6 towards the second end/back of the beveled platform 7 in the direction of the Y-axis (shown in FIG. 17). In one embodiment, said beveled platform 5 increases in thickness from said first side 8 towards the second side 9 in the direction of the X-axis (shown in FIG. 18). In one embodiment, said beveled platform 5 increases in thickness from said first side 8 towards the second side 9 in the direction of the X-axis and said beveled platform 5 increases in thickness from a fine blade tip of the first end 6 towards the second end/back of the beveled platform 7 in the direction of the Y-axis (shown in FIG. 18). In one embodiment, said first blade 10 and said second blade 11 are parallel (shown in FIG. 15). In one embodiment, said first blade 10 and said second blade 11 extend above the top surface of said second end/back of the beveled platform 7. In one embodiment, said first blade 10 and said second blade 11 are positioned at an angle between approximately 100 to 140 degrees relative to the top surface of said second end/back of the beveled platform 7 (shown in FIG. 15). In one embodiment, said beveled platform 5 is approximately 0.3 millimeters wide. In one embodiment, said beveled platform 5 is approximately 0.2 millimeters wide. In a preferred embodiment, said beveled platform 5 is approximately 0.25 millimeters wide. In one embodiment, said beveled platform 5 is approximately 1.0 millimeters long. In one embodiment, said beveled platform 5 is approximately 0.4 millimeters high. In one embodiment, said highest point on the beveled platform 5 is the first and second blades. The device 12 (shown in FIG. 8, FIG. 10, FIG. 13, and FIG. 15) may be provided as a pre-sterilized, single-use disposable probe or tip that is attachable to a standard surgical handpiece.

It is not intended that embodiments of the invention be limited to any particular construction material; however, it is believed that preferred materials include titanium, stainless steel, polyether ether ketone (PEEK), shape memory alloy, and shape memory polymers. In one embodiment, the present device is made from metal alloy materials described by Furst, J. G. et al. "Metal Alloys for Medical Devices," U.S. Pat. No. 7,648,591 [40], Richter, K. "Amorphous Metal Alloy Medical Devices," U.S. Pat. No. 7,955,387 [41], all herein incorporated by reference. In one embodiment, the present device is made from a shape memory polymer materials described by Shandas, R. et al. "Shape Memory Polymer Medical Devices," U.S. patent application Ser. No. 12/295,594 [42], Reimink, M. S. and Ogle, M. F. "Medical Devices with Polymer/Inorganic Substrate Composites," U.S. Pat. No. 7,604,663 [43], Langer, R. S. and Lendlein, A. "Shape Memory Polymers," U.S. Pat. No. 6,388,043 [44], Langer, R. S. and Lendlein, A. "Shape Memory Polymers," U.S. Pat. No. 6,720,402 [45], Tong, T. H. "Shape Memory Styrene Copolymer," U.S. Pat. No. 6,759,481 [46], Stalker, K. C. B. et al. "Variable Stiffness Medical Devices," U.S. Pat. No. 7,632,303 [47], Anthamatten, M. L. and Li, J. "Shape Memory Polymers," U.S. Pat. No. 7,935,131 [48], and Berger, E. J. et al. "Methods of Forming a Part Using Shape Memory Polymers," U.S. Pat. No. 8,038,923 [49], all herein incorporated by reference. In some embodiments, the device of the current invention is rigid at room temperature, but is more flexible at body temperature. In some embodiments, the portions of the device of the current invention are rigid at room temperature, but are more flexible at body temperature. In some embodiments, portions of the device are made from different materials. In some embodiments, portions of the device are made from materials of various rigidity. In one embodiment, said tool shaft is flexible. In some embodiments, said tool shaft is made from a lower density material.

It is not intended that embodiments of the invention be limited to any particular construction material; however, it is believed that preferred materials include titanium, stainless steel, polyether ether ketone (PEEK), shape memory alloy, and shape memory polymers. In some embodiments, the device of the current invention is rigid at room temperature, but is more flexible at body temperature. In some embodiments, the portions of the device of the current invention are rigid at room temperature, but are more flexible at body temperature. In some embodiments, portions of the device are made from different materials. In some embodiments, portions of the device are made from materials of various rigidity. In one embodiment, said tool shaft is flexible. In some embodiments, said tool shaft is made from a lower density material.

Figure 10:
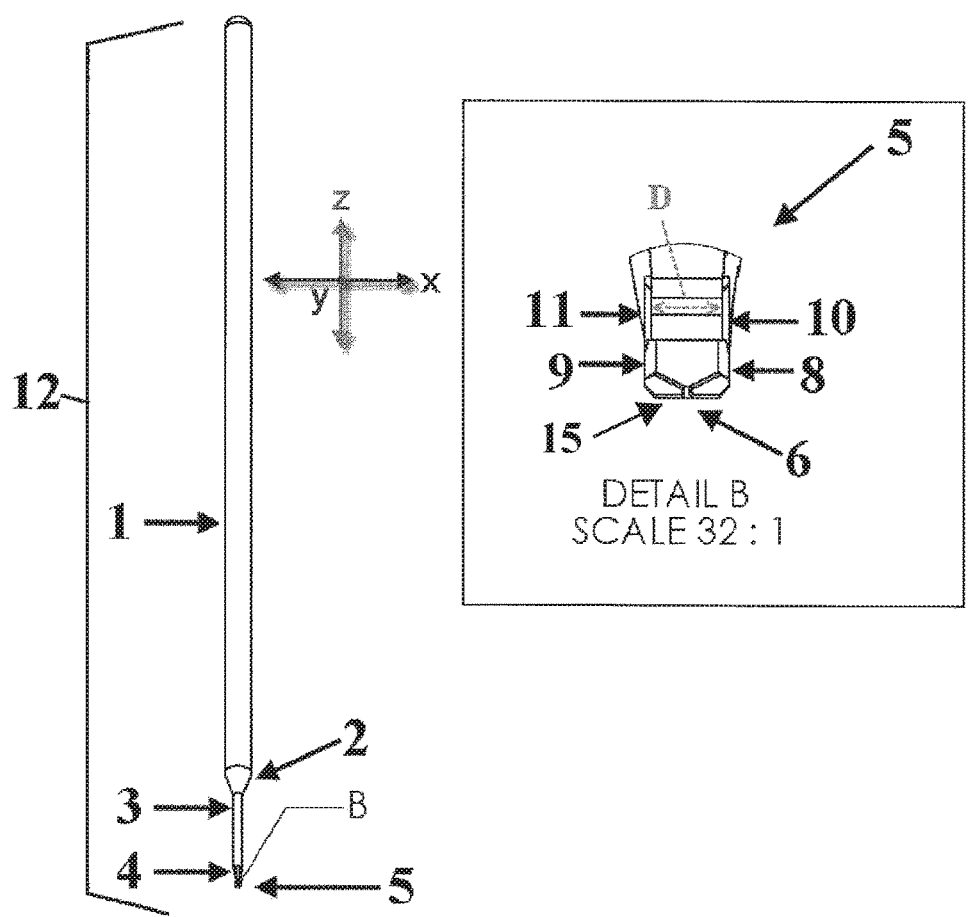
FIG. 10 shows a front face view of one embodiment of the device with an enlarged detailed view of the operative end of the device with the beveled platform.
Figure 11:
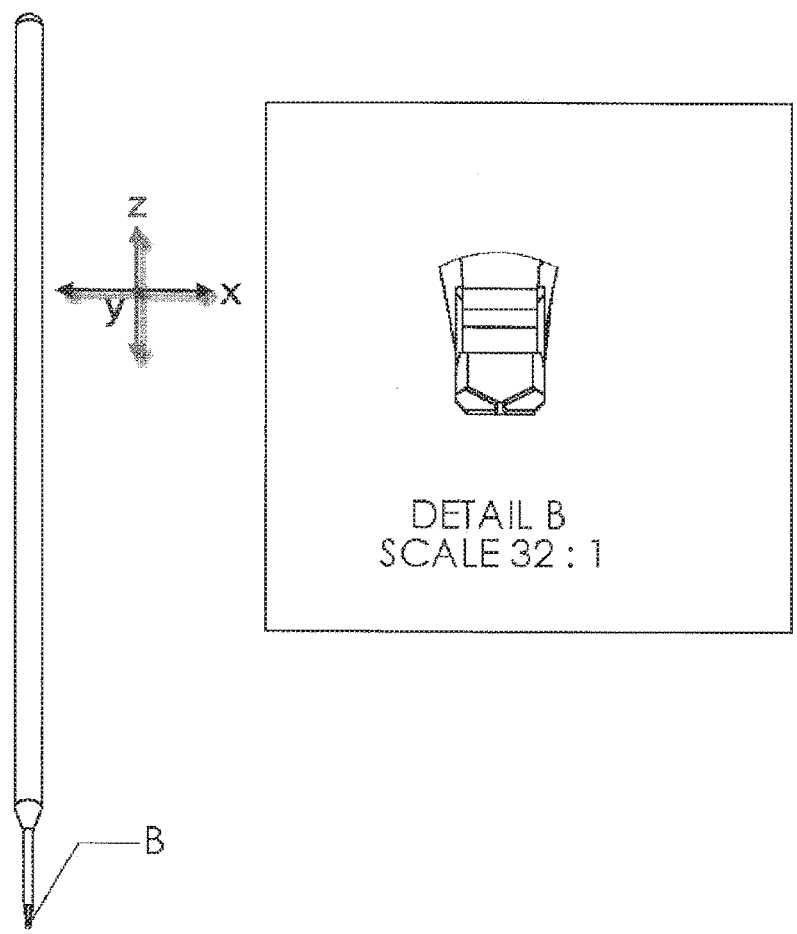
FIG. 11 shows a front face view of one embodiment of the device with an enlarged detailed view of the operative end of the device with the beveled platform 5. Measurements of specific parts are indicated.
Figure 12:
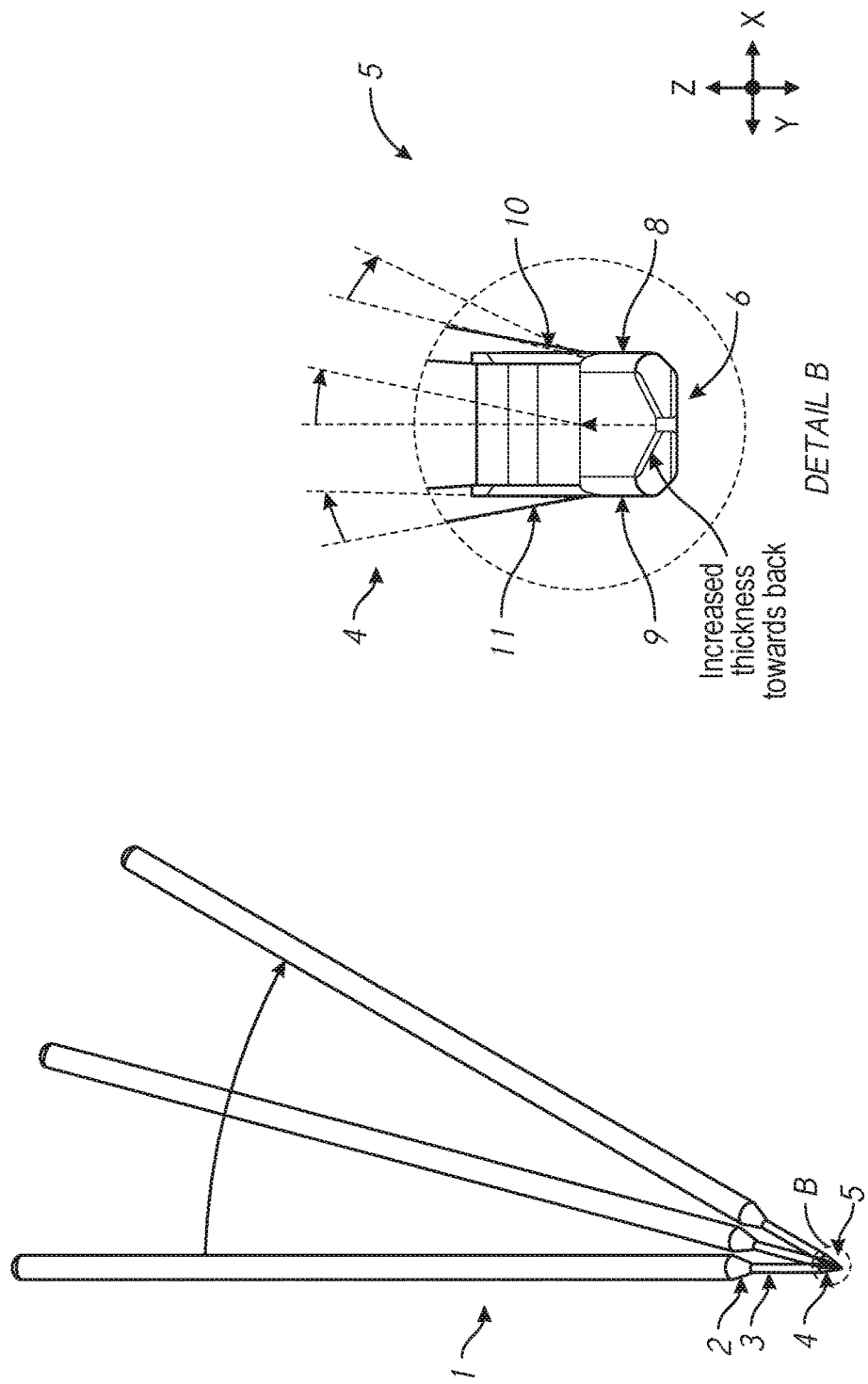
FIG. 12 shows a front face view of one embodiment of the device with an enlarged detailed view of the operative end of the device with the beveled platform 5. Shown are examples of the different angles of attachment of the handle 1 to the beveled platform 5 relative to the Z-axis. The increased platform thickness as the platform extends from the insertion tip 6 towards the back of the platform 7 is also indicated.
Figure 13:
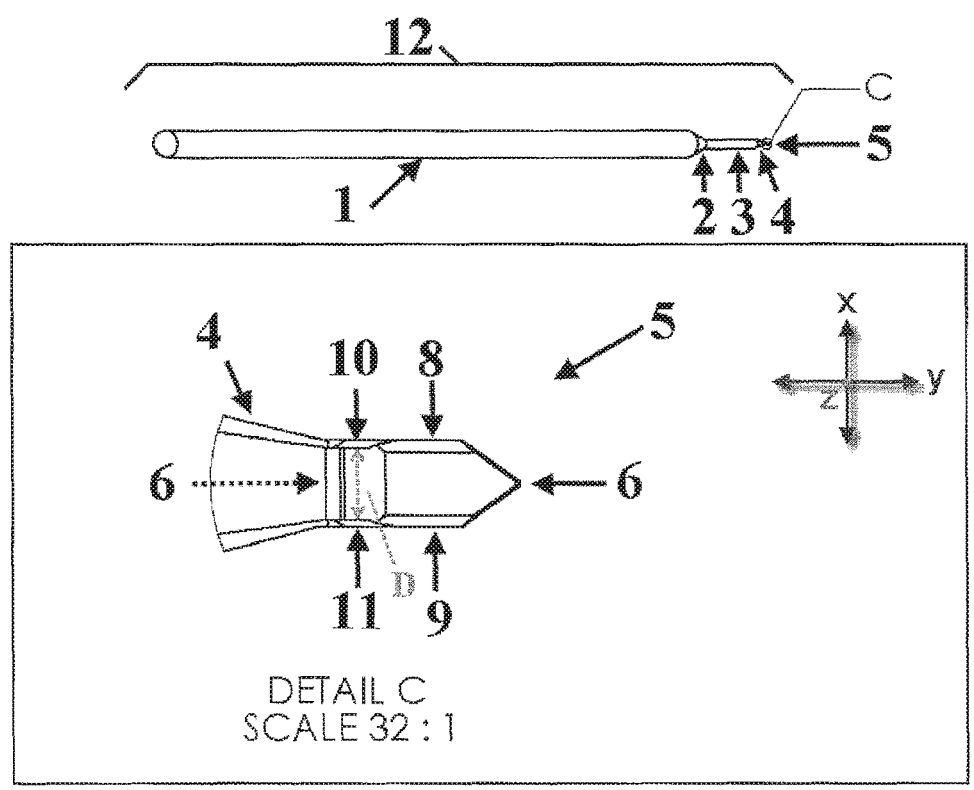
FIG. 13 shows a straight top view of one embodiment of the device with an enlarged detailed view of the operative end of the device with the beveled platform 5.
Figure 14:
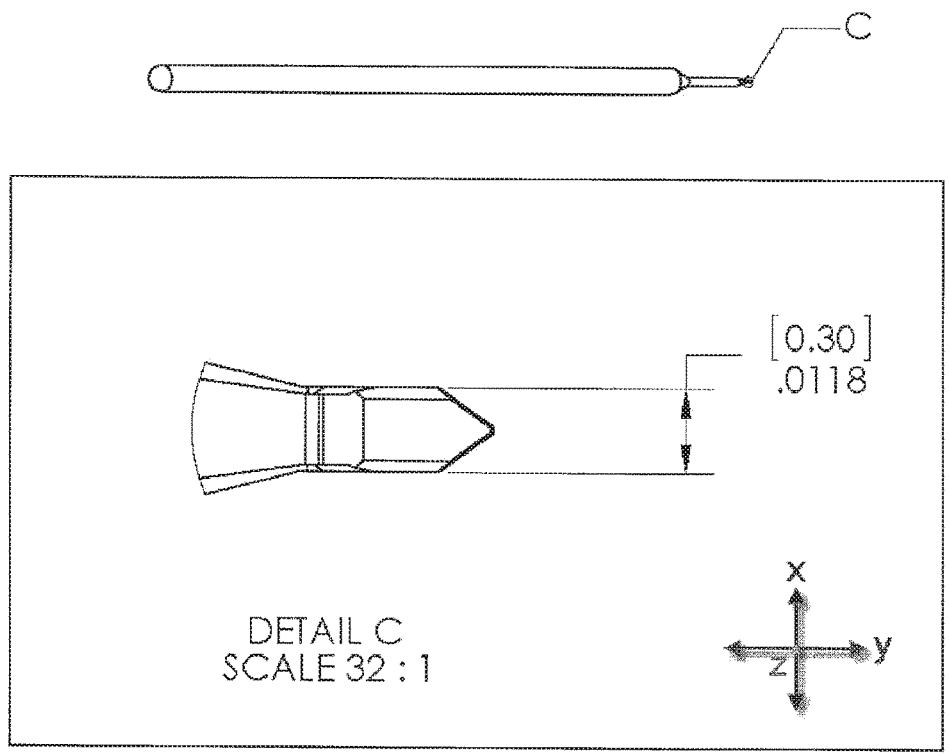
FIG. 14 shows a straight top view of one embodiment of the device with an enlarged detailed view of the operative end of the device with the beveled platform 5. Measurements of specific parts are indicated.
Figure 15:
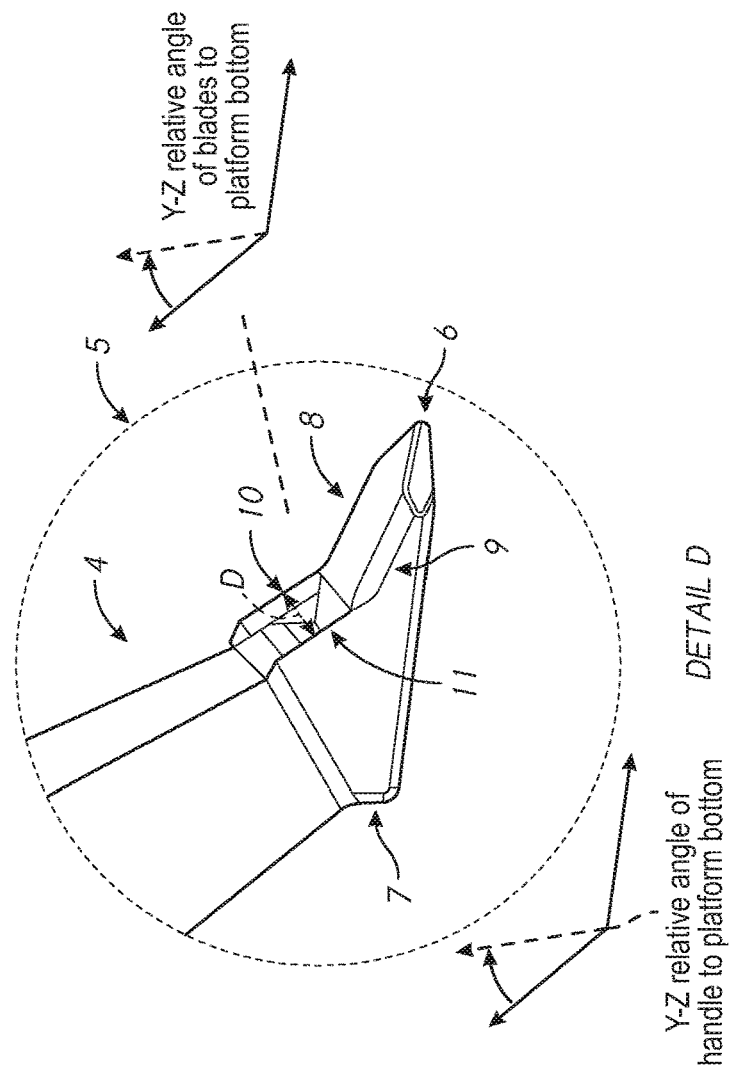
FIG. 15 shows an angled, side view of one embodiment of the device with an enlarged detailed view of the operative end of the device with the beveled platform 5. The shaded aspect provided a view of the dimensions of the beveled platform. The angle of tool shaft 4 attachment and of first and second blade attachment relative to the beveled platform 5 are indicated.
Figure 15:
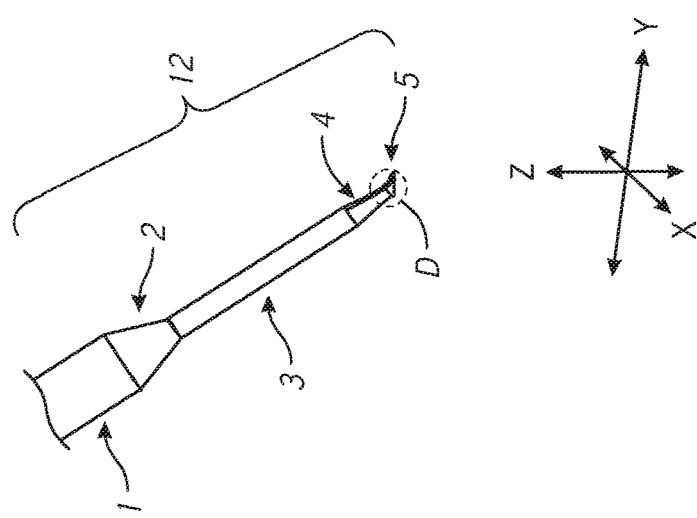
Figure 16:
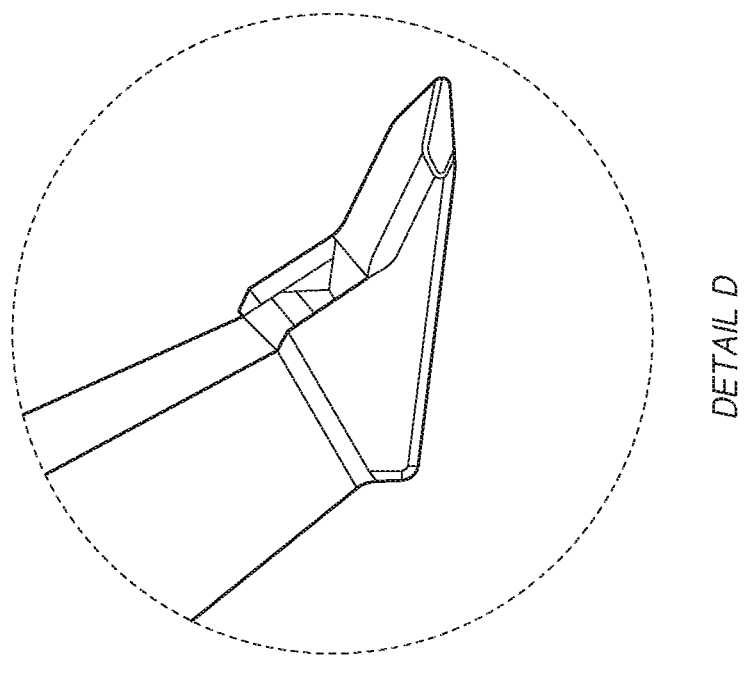
FIG. 16 shows an angled, side view of one embodiment of the device with an enlarged detailed view of the operative end of the device with the beveled platform 5. The shaded aspect provided a view of the dimensions of the beveled platform. Measurements of specific parts are indicated.
Figure 16:
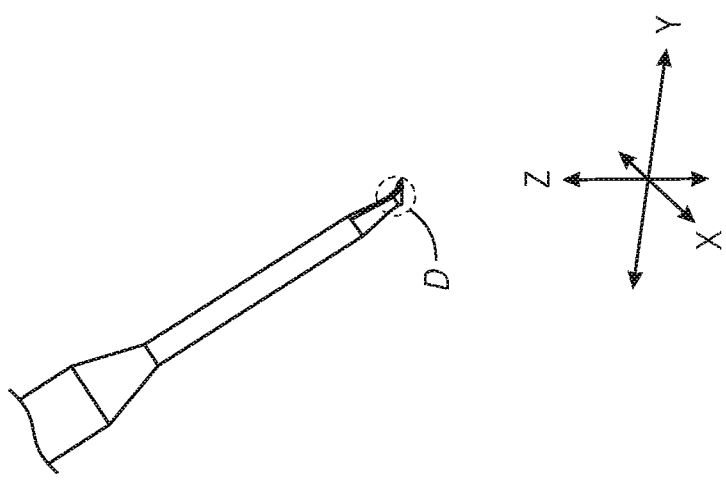

In one embodiment, the invention relates to a method for cutting a strip of tissue of width W from a tissue mass, said method comprising the steps of: a) providing a device which comprises; i) a handle attached to a beveled platform, ii) an anterior insertion blade tip of the beveled platform expanding backwards to a posterior end of the beveled platform, iii) a first side of the beveled platform upon which is affixed a first lateral blade, iv) a second side of the beveled platform upon which is affixed a second lateral blade; v) at least first and second lateral cutting edges formed by blades in a generally perpendicular and posterior position to said opposite edges of said anterior insertion blade tip of the beveled platform, said first and second cutting edges being separated by a distance D that is approximately equal to the width W of the strip of tissue to be cut (this is shown in FIG. 10, FIG. 13, and FIG. 15); b) advancing the anterior insertion blade tip of the beveled platform through tissue such that the first and second cutting edges are positioned adjacent to tissue to be cut; c) advancing the distal end such that the cutting edges cut a strip of tissue of approximate width W and the cut strip of tissue remains substantially intact. In one embodiment, the mass of tissue is in vivo. In one embodiment, the mass of tissue is in vitro. In one embodiment, the mass of tissue is located within the body of a human or animal subject. In one embodiment, the strip of tissue is removed for a diagnostic or therapeutic purpose. In one embodiment, the subject suffers from glaucoma and wherein the method is carried out to remove a strip of trabecular meshwork from an eye of the subject to facilitate drainage of aqueous humor from the eye thereby lowering intraocular pressure. In one embodiment, step b comprises inserting the device into the anterior chamber of the eye; positioning the anterior insertion blade tip of the beveled platform adjacent to or within the trabecular meshwork of the eye; and advancing the cutting tube such that the cutting edges cut a strip of approximate width W from the trabecular meshwork. In one embodiment, the device provided in step a of the method further comprises an anterior insertion blade tip of the beveled platform and wherein the anterior insertion blade tip of the beveled platform is advanced through the trabecular meshwork and into Schlemm's canal and, thereafter, the anterior insertion blade tip of the beveled platform is advanced through Schlemm's canal as the cutting tube is advanced to cut the strip of tissue. In one embodiment, the device provided in step a further comprises apparatus for severing the strip of tissue after the strip of tissue has reached a desired length and wherein the method further comprises the step of severing the strip of tissue after the strip of tissue has reached a desired length. In one embodiment, the method is carried out to form an incision in skin, mucous membrane, an organ, a tumor or other anatomical structure. In one embodiment, the method is carried out to remove tissue from the vascular system. In one embodiment, the method is carried out to remove tissue from the lymphatic system. In one embodiment, the invention further comprises the step of: c) removing the strip of tissue.

It is not intended that embodiments of the invention be limited to any particular method, medical target, or device confirmation; however, it is believed that the device may be optimally designed to remove trabecular meshwork of the eye, unroofing small vessels (such as veins, arteries, lymphatic vessels, or other vessel with a lumen), and for creating a hole or opening in the tympanic membrane of the ear. It is not intended that embodiments of the invention be limited to any particular mechanism; however, it is believed that creating an opening in the tympanic membrane of the ear may help aid in treating ear disease.

It is not intended that embodiments of the invention be limited to any particular endoscope, it is believed that the device may be optimally designed for an ophthalmic endoscopy system endoscope. One such system is commercially called "Endo Optiks."

Thus, specific compositions and configurations of a modified dual-blade cutting system have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

REFERENCES

1. Kahook, M. Y. "Modified Dual-Blade Cutting System," United States Provisional Patent application 61/637,611, filed Apr. 24, 2012. (published N/A).
2. Baerveldt, G. and Chuck, R. "Minimally Invasive Glaucoma Surgical Instrument and Method," U.S. Pat. No. 6,979,328, application Ser. No. 10/052,473, filed Jan. 18, 2002. (issued Dec. 27, 2005).
3. Baerveldt, G and Chuck, R. "Minimally Invasive Glaucoma Surgical Instrument and Method," United States Patent Application Publication Number 20110077626, application Ser. No. 12/843,458, filed Jul. 26, 2010. (published Mar. 31, 2011).
4. Baerveldt, G and Chuck, R. "Minimally Invasive Glaucoma Surgical Instrument and Method," United States Patent Application Publication Number 20060106370, application Ser. No. 11/273,914, filed Nov. 14, 2005. (published May 18, 2006).

5. Baerveldt, G. and Chuck, R. "Minimally Invasive Glaucoma Surgical Instrument and Method," United States Patent Application Publication Number 20020111608, application Ser. No. 10/052,473, filed Jan. 18, 2002. (published Aug. 15, 2002).

6. Baerveldt, G and Chuck, R. "Minimally Invasive Glaucoma Surgical Instrument and Method," U.S. Pat. No. 7,785,321, application Ser. No. 11/273,914, filed Nov. 14, 2005. (issued Aug. 31, 2010).

7. Quigley, H. A. and Broman, A. T. (2006) "The number of people with glaucoma worldwide in 2010 and 2020," *Br. J. Ophthalmol.* 90(3), 262-267.

8. Grant, W. M. (1951) "Clinical measurements of aqueous outflow," *A.M.A. Archives of Ophthalmology* 46(2), 113-131.

9. Grant, W. (1963) "Experimental aqueous perfusion in enucleated human eyes," *Arch. Ophthalmol.* 69(6), 783-801.

10. Johnson, D. H. and Tschumper, R. C. (1987) "Human trabecular meshwork organ culture. A new method," *Invest. Ophthalmol. Vis. Sci.* 28(6), 945-953.

11. Herschler, J. and Davis, E. B. (1980) "Modified goniotomy for inflammatory glaucoma. Histologic evidence for the mechanism of pressure reduction," *Arch. Ophthalmol.* 98(4), 684-687.

12. Luntz, M. H. and Livingston, D. G (1977) "Trabeculotomy ab externo and trabeculectomy in congenital and adult-onset glaucoma," *Am. J. Ophthalmol.* 83(2), 174-179.

13. Anderson, D. R. (1983) "Trabeculotomy compared to goniotomy for glaucoma in children," *Ophthalmology* 90(7), 805-806.

14. Jea, S. Y. et al. (2012) "Ab Intern Trabeculectomy Versus Trabeculectomy for Open-Angle Glaucoma," *Ophthalmology* 119(1), 36-42.

15. Minckler, D. S. et al. (2005) "Clinical Results with the Trabectome® for Treatment of Open-Angle Glaucoma," *Ophthalmology* 112(6), 962-967.

16. Pantcheva, M. B. and Kahook, M. Y. (2010) "Ab Interno Trabeculectomy," *Middle East Afr. J. Ophthalmol.* 17(4), 287-289.

17. Francis, B. A. et al. (2006) "Ab interno trabeculectomy: development of a novel device (Trabectome®) and surgery for open-angle glaucoma," *J. Glaucoma* 15(1), 68-73.

18. Tan, Y., Tsou, P., and Tan, G. S. (2011) "Postoperative complications after glaucoma surgery for primary angle-closure glaucoma vs primary open-angle glaucoma," *Arch. Ophthalmol.* 129(8), 987-992.

19. Seibold, L. K. et al. (2013) "Preclinical Investigation of Ab Interno Trabeculectomy Using a Novel Dual-Blade Device," *Am. J. Ophthalmol.* 155(3), 524-529.e522.

20. Jacobi, P. C., Dietlein, T. S., and Krieglstein, G K. (1997) "Technique of goniocurettage: a potential treatment for advanced chronic open angle glaucoma," *Br J. Ophthalmol.* 81(4), 302-307.

21. Jacobi, P. C., Dietlein, T. S., and Krieglstein, G K. (1999) "Goniocurettage for removing trabecular meshwork: clinical results of a new surgical technique in advanced chronic open-angle glaucoma," *Am. J. Ophthalmol.* 127(5), 505-510.

22. Ting, J. L. M., Damji, K. F., and Stiles, M. C. (2012) "Ab interno trabeculectomy: Outcomes in exfoliation versus primary open-angle glaucoma," 0.1 Cataract. Refract. Surg. 38(2), 315-323.

23. Sorensen, J. T., Mittelstein, M., and Mirhashemi, S. "Tubular Cutter Device and Methods For Cutting and Removing Strips of Tissue from the Body of a Patient," U.S. Pat. No. 7,959,641, application Ser. No. 10/560,267, filed Jun. 10, 2004. (issued Jun. 14, 2011).

24. Sorensen, J., T., Mittelstein, M., and Mirhashemi, S. "Tubular Cutting Device for Cutting and Removing Tissue," WIPO PCT Patent Publication Number WO/2004/110501, Application PCT/US2004/018488, filed Jun. 10, 2004. (published Dec. 23, 2004).

25. Sorensen, J. T., Mittelstein, M., and Mirhashemi, S. "Tubular Cutter Device And Methods For Cutting And Removing Strips Of Tissue From The Body Of A Patient," United States Patent Application Publication Number 20070276420, application Ser. No. 10/560,267, filed Jun. 10, 2004. (published Nov. 29, 2007).

26. Huculak, J. C. "Small Gauge Mechanical Tissue Cutter/Aspirator Probe For Glaucoma Surgery," United States Patent Application Publication Number 20090287233, application Ser. No. 12/120,867, filed May 15, 2008. (published Nov. 19, 2009).

27. Lind, C. and Huculak, J. C. "Small Gauge Mechanical Tissue Cutter/Aspirator Probe For Glaucoma Surgery," WIPO PCT Patent Publication Number WO/2009/140185, Application PCT/US2009/043420, filed May 11, 2009. (published Nov. 19, 2009).

28. Lind, C. and Huculak, J. C. "Small Gauge Mechanical Tissue Cutter/Aspirator Probe For Glaucoma Surgery," European Patent EP 2303203, Application EP 09747269.0, filed May 11, 2009. (published Apr. 6, 2011).

29. Bergheim, O. B. and Gharib, M. "Apparatus and Method for Treating Glaucoma," WIPO PCT Patent Publication Number WO/2001/078631, Application PCT/US2001/007398, filed Mar. 8, 2001. (published Oct. 25, 2001).

30. Skjaerpe, F. "Microsurgical instrument," U.S. Pat. No. 4,501,274, application Ser. No. 06/438,891, filed Oct. 29, 1982. (issued Feb. 26, 1985).

31. Skjaerpe, F. "Microsurgical instrument," European Patent EP 0073803 B1, Application EP 82900833, filed Mar. 12, 1982. (issued Jul. 10, 1985).

32. Conston, S. R. and Yamamoto, R. K. "Ophthalmic microsurgical system," United States Patent Application Publication Number 20060149194, application Ser. No. 10/496,254, filed Nov. 21, 2002. (published Jul. 6, 2006).

33. Conston, S. R. and Yamamoto, R. K. "Ophthalmic microsurgical system," WIPO PCT Patent Publication Number WO/2003/045290, Application PCT/US2002/037572, filed Nov. 21, 2002. (published Jun. 5, 2003).

34. Conston, S. R. and Yamamoto, R. K. "Ophthalmic microsurgical system," European Patent EP 1455698 A1, Application EP 02791298 A, filed Nov. 21, 2002. (published Sep. 15, 2004).

35. Conston, S. R. and Yamamoto, R. K. "Ophthalmic microsurgical system," Korean Patent KR 1020040058309, Application KR 1020040058309, filed Nov. 21, 2002. (issued Sep. 15, 2004).

36. Conston, S. R. and Kupiecki, D. J. "Ophthalmic microsurgical instruments," United States Patent Application Publication Number 20070073275, application Ser. No. 10/555,065, filed Apr. 16, 2004. (published Mar. 29, 2007).

37. Conston, S. R. et al. "Ophthalmic Microsurgical Instruments," WIPO PCT Patent Publication Number WO/2004/093761, Application PCT/US2004/011783, filed Apr. 16, 2004. (published Nov. 4, 2004).
38. Conston, S. R. et al. "Ophthalmic Microsurgical Instruments," European Patent EP 1615604 A1, Application EP 04750224.0, filed Apr. 16, 2004. (published Jan. 18, 2006).
39. Huculak, J. C., Kovalcheck, S., and Lind, C. "Pulsed Electric Field Probe for Glaucoma Surgery," United States Patent Application Publication Number 20110230877, application Ser. No. 12/725,020, filed Mar. 16, 2010. (published Sep. 22, 2011).
40. Furst, J. G, Patel, U., and Buckman. Jr., R. W. "Metal alloys for medical devices," U.S. Pat. No. 7,648,591, application Ser. No. 12/272,317, filed Nov. 17, 2008. (issued Jan. 19, 2010).
41. Richter, K. "Amorphous metal alloy medical devices," U.S. Pat. No. 7,955,387, application Ser. No. 12/243,741, filed Oct. 1, 2008. (issued Jun. 7, 2011).
42. Shandas, R. et al. "Shape Memory Polymer Medical Devices," United States Patent Application Publication Number 20090248141, application Ser. No. 12/295,594, filed Mar. 30, 2007. (published Oct. 1, 2009).
43. Reimink, M. S. and Ogle, M. F. "Medical devices with polymer/inorganic substrate composites," U.S. Pat. No. 7,604,663, application Ser. No. 09/475,721, filed Dec. 30, 1999. (issued Oct. 20, 2009).
44. Langer, R. S. and Lendlein, A. "Shape memory polymers," U.S. Pat. No. 6,388,043, application Ser. No. 09/256,626, filed Feb. 23, 1999. (issued May 14, 2002).
45. Langer, R. S. and Lendlein, A. "Shape memory polymers," U.S. Pat. No. 6,720,402, application Ser. No. 10/141,891, filed May 8, 2002. (issued Apr. 13, 2004).
46. Tong, T. H. "Shape memory styrene copolymer," U.S. Pat. No. 6,759,481, application Ser. No. 10/056,590, filed Jan. 24, 2002. (issued Jul. 6, 2004).
47. Stalker, K. C. B. et al. "Variable stiffness medical devices," U.S. Pat. No. 7,632,303, application Ser. No. 10/152,150, filed May 21, 2002. (issued Dec. 15, 2009).
48. Anthamatten, M. L. and Li, J. "Shape memory polymers," U.S. Pat. No. 7,935,131, application Ser. No. 11/820,693, filed Jun. 20, 2007. (issued May 3, 2011).
49. Berger, E. J. et al. "Methods of forming a part using shape memory polymers," U.S. Pat. No. 8,038,923, application Ser. No. 12/356,518, filed Jan. 20, 2009. (issued Oct. 18, 2011).

I claim:

1. An ophthalmic device comprising:
a handle;
a tool shaft connected to the handle;
a platform connected to the tool shaft, wherein the platform comprises:
an insertion tip on a distal end of the platform;
a posterior end;
a bottom surface;
a top surface that is planar;
a first lateral side;
a second lateral side, wherein the bottom surface, the top surface, the first lateral side, and the second lateral side extend from the insertion tip towards the posterior end, the first lateral side and the second lateral side being perpendicular to the bottom surface;
a first lateral blade extending from the first lateral side; and
a second lateral blade extending from the second lateral side, the first lateral blade and the second lateral blade (i) separated by a gap defining an unoccupied space and (ii) connecting the top surface to the tool shaft, such that the top surface is configured to guide trabecular meshwork to the first lateral blade and the second lateral blade.

2. The device of claim 1, wherein the first lateral blade and the second lateral blade are in a perpendicular alignment to a bottom of the platform.

3. The device of claim 1, wherein the platform is set at a specific angle and orientation relative to the handle.

4. The device of claim 1, wherein the handle and platform are operably attached at an angle ranging between 90 and 120 degrees in the Y-Z plane.

5. The device of claim 1, wherein the handle and the platform are operably attached at an angle ranging between 90 and 180 degrees in the X-Z plane.

6. The device of claim 1, wherein the platform freely rotates relative to the handle in a dimension selected from the group consisting of an X-Y dimension and a positive Z dimension.

7. The device of claim 1, wherein the platform remains at a fixed angle in the X-Y, X-Z, and Y-Z dimensions relative to the handle.

8. The device of claim 1, wherein a height of the platform is not to exceed 0.5 millimeters.

9. The device of claim 1, wherein a length of the platform from the insertion tip to the posterior end of the platform is not to exceed 1.0 millimeters.

10. The device of claim 1, wherein the platform increases in thickness from the insertion tip towards the posterior end of the platform in the direction of the Y-axis.

11. The device of claim 1, wherein the first lateral blade is attached to a first side of the posterior end of the platform.

12. The device of claim 1, wherein the first lateral blade and platform are operably attached at an angle ranging between 90 and 180 degrees in the Y-Z plane.

13. The device of claim 1, wherein the second lateral blade and the platform are operably attached at an angle ranging between 90 and 120 degrees in the Y-Z plane.

14. The device of claim 1, wherein the first lateral blade and the handle are operably positioned at an angle ranging between 90 and 120 degrees in the Y-Z plane.

15. The device of claim 1, wherein the second lateral blade and the handle are operably positioned at an angle ranging between 90 and 120 degrees in the Y-Z plane.

16. The device of claim 1, wherein the second lateral blade is attached to a second side of the posterior end of the platform.

17. The device of claim 1, wherein the first lateral blade and the second lateral blade are parallel.

18. The device of claim 1, wherein the first lateral blade and the second lateral blade extend above a top surface of the posterior end of the platform.

19. The device of claim 1, wherein the first lateral blade and the second lateral blade are positioned at an angle between approximately 100 to 140 degrees in the Y-Z plane relative to a bottom surface of the posterior end of the platform.

20. The device of claim 1, wherein the device is made from at least one of the following materials: titanium, stainless steel, polyether ether ketone, shape memory alloy, and shape memory polymers.

21. The device of claim 1, wherein the tool shaft is flexible.

22. The device of claim 1, wherein the tool shaft is made from a lower density material relative to the platform.

* * * * *